(12) United States Patent
Nienaber et al.

(10) Patent No.: US 6,297,021 B1
(45) Date of Patent: Oct. 2, 2001

(54) LIGAND SCREENING AND DESIGN BY X-RAY CRYSTALLOGRAPHY

(75) Inventors: Vicki L. Nienaber, Gurnee; Jonathan Greer, Chicago; Celerino Abad-Zapatero, Lake Forest; Daniel W. Norbeck, Grayslake, all of IL (US)

(73) Assignee: Abbott Laboratories, Abbott Park, IL (US)

( * ) Notice: Subject to any disclaimer, the term of this patent is extended or adjusted under 35 U.S.C. 154(b) by 0 days.

(21) Appl. No.: 09/263,904

(22) Filed: Mar. 5, 1999

Related U.S. Application Data

(63) Continuation-in-part of application No. 09/036,184, filed on Mar. 6, 1998.

(51) Int. Cl.$^7$ .............................. G01N 33/53; C30B 29/58

(52) U.S. Cl. ............................................. 435/7.1; 117/927

(58) Field of Search ............................... 435/7.1; 117/927

(56) References Cited

U.S. PATENT DOCUMENTS 5,112,755  5/1992  Heyneker et al. .................... 435/215

OTHER PUBLICATIONS

Schevitz et al., "Structure–Based Design of the First Potent and Selective Inhibitor of Human Non–Pancreatic Secretory Phospholipase A2", Nature Struct. Biol., 2(6), 458–465, Jun. 1995.*

Chen et al., "3–D Structure of a Mutant (Asp 101–Ser) of E. coli Alkaline Phosphatase with Higher Catalytic Activity", Prot. Eng., 5(7), 605–610, Oct. 1992.*

Thunnissen et al., "X–Ray Structure of Phospholipase A2 Complexed with a Substrate–Derived Inhibitor", Nature, 347(6294), 689–691, Oct. 1990.*

J. Zheng, et al., Biochemistry, vol. 32, No. 9, pp. 2154–2161, 1993.

A. Hausrath, et al., The Journal of Biological Chemistry, vol. 269, No. 29, Issue of Jul. 22, pp. 18839–18842, 1994.

(List continued on next page.)

Primary Examiner—Jon P. Weber
(74) Attorney, Agent, or Firm—Daniel W. Collins

(57) ABSTRACT

X-ray crystallography can be used to screen compounds that are not known ligands of a target biomolecule for their ability to bind the target biomolecule. The method includes obtaining a crystal of a target biomolecule; exposing the target biomolecule crystal to one or more test samples; and obtaining an X-ray crystal diffraction pattern to determine whether a ligand/receptor complex is formed.

The target is exposed to the test samples by either co-crystallizing a biomolecule in the presence of one or more test samples or soaking the biomolecule crystal in a solution of one or more test samples. In another embodiment, structural information from ligand/receptor complexes are used to design ligands that bind tighter, that bind more specifically, that have better biological activity or that have better safety profile.

A further embodiment of the invention comprises identifying or designing biologically-active moieties by the instant process.

In a further embodiment, a biomolecule crystal having an easily accessible active site is formed by co-crystallizing the biomolecule with a degradable ligand and degrading the ligand.

22 Claims, 14 Drawing Sheets

OTHER PUBLICATIONS

Verlinde, et al., "Antitrypanosomiasis Drug Development Based on Structures of Glycolytic Enzymes", Structured–Based Drug Design, 1997, Chapter 15, pp. 365–394.
J. Hajdu, et al., Nature, vol. 329, pp. 178–181, 1987.
P.M. Colman, Current Opinion in Structural Biology, vol. 4, pp. 868–874, 1994.
J. Greer, et al., Journal of Medicinal Chemistry, vol. 37, No. *, pp. 1035–1054, 1994.
C. Verlinde, et al., Structure, vol. 2, pp. 577–587, 1984.
S. B. Shuker, et al., Science, vol. 274, pp. 1531–1534, 1996.
C. Verlinde, et al., Journal of Computer–Aided Molecular Design, vol. 6, pp. 131–147, 1992.
P. Verde, et al., Proc. Natl. Acad. Sci. USA, vol. 81, pp. 4727–4731, 1984.
M. Nagai, et al., Gene, vol. 36 (1–2), pp. 183–188, 1985.
G. Spraggon, et al., Structure, vol. 3 No. 7, pp. 681–691, 1995.
T. J. Pilot–Matias, et al., Gene, vol. 128, pp. 219–225, 1993.
A. Granelli–Piperno, et al., J. Exp. Med., vol. 148, pp. 223–234, 1978.
J. Vialard, et al., Journal of Virology, vol. 64(1), pp. 37–50, 1990.
G. Claeson, et al., Haemostasis, vol., 7, pp. 76–78, 1978.
E. Menegatti, et al., J. Enzyme Inhibition, vol. 2, pp. 249–259, 1989.
J. Navaza, Acta Crystallographica, A50, pp. 157–163, 1994.
K. Allen, et al., J. Phys. Chem. 1996 100, pp. 2605–2611.
Ford et al., "Crystal Structure of a Lysozyme–Tetrasaccharide Lactone Complex," J. Mol. Biol. 1974, vol. 88, pp. 349–371.
Alber et al., "Crystal Structure of Elastase–Substrate Complex at –55° C," Nature, Sep. 23, 1976, vol. 263, No. 5575, pp. 297–300.
Fink et al., "X–Ray Cryoenzymology," Adv. Enz A. Meister Ed Wiley & Sons. New York, 1981, vol. 52, pp. 177–246.
Howell et al., "Functional Role of Aspartic Acid–27 in Dihydrofolate Reductase Revealed by mutagenesis," Science, Mar. 7, 1986, vol. 231, pp. 1123–1128.
Verlinde et al., "In Search of New Lead Compounds for Trypanosomiasis Drug Design: Protein Structure–Based Linked–Fragment Approach," J. Computer–Aided Mol. Des., Apr. 1992, vol. 6, No. 2, pp. 131–147.
Thaisrivongs et al., "Structure–Based Design of HIV Protease Inhibitors: 5,6–Dihydro–4–hydroxy–2–pyrones as Effective, Nonpeptidic Inhibitors," J. Med. Chem., Nov. 8, 1996. vol. 39, No. 23, pp. 4630–4642.

* cited by examiner

A.

B.

LIGAND SCREENING AND DESIGN BY X-RAY CRYSTALLOGRAPHY

CROSS REFERENCE TO RELATED APPLICATIONS

This application is a continuation in part of Ser. No. 09/036,184, filed Mar. 6, 1998, now abandoned.

TECHNICAL FIELD OF THE INVENTION

X-ray crystallography is useful for identifying ligands that bind target receptor molecules and for designing ligands with improved biological activity for the target receptor.

BACKGROUND OF THE INVENTION

X-ray crystallography (crystallography) is an established, well-studied technique that provides what can be best described as a three-dimensional picture of what a molecule looks like in a crystal. Scientists have used crystallography to solve the crystal structures for many biologically important molecules. Many classes of biomolecules can be studied by crystallography, including, but not limited to, proteins, DNA, RNA and viruses. Scientists have even reported the crystal structures of biomolecules that carry ligands within its receptors (a "ligand-receptor complex").

Given a "picture" of a target biomolecule or a ligand-receptor complex, scientists can look for pockets or receptors where biological activity can take place. Then scientists can experimentally or computationally design high-affinity ligands (or drugs) for the receptors. Computational methods have alternatively been used to screen for the binding of small molecules. However, these previous attempts have met with limited success. Several problems plague ligand design by computational methods. Computational methods are based on estimates rather than exact determinations of the binding energies, and rely on simple calculations when compared with the complex interactions that exist within a biomolecule. Moreover, computational models require experimental confirmation which often expose the models as false positives that do not work on the real target.

Moreover, experimental high-affinity ligand design based on a "picture" of the ligand-receptor complex has been limited to biomolecules that already have known ligands. Finally, scientists only recently reported the crystallographic study of interactions between organic solvents and target biomolecules. Allen et al., *J. Phys. Chem.*, v. 100, pp. 2605–11 (1996). However, these studies are limited to mapping solvent sites rather than ligand sites. It would be desirable to directly identify potential ligands, and to obtain detailed information on how the ligand binds and changes in the target biomolecule. In addition, methods for identifying and/or designing ligands which possess biological and/or pharmaceutical activity with respect to a given target molecule would be desireable.

BRIEF SUMMARY OF THE INVENTION

Crystallography can be used to screen and identify compounds that are not known ligands of a target biomolecule for their ability to bind the target. The method (hereinafter "CrystaLEAD™") comprises obtaining a crystal of a target biomolecule; exposing the target to one or more test samples that are potential ligands of the target; and determining whether a ligand/biomolecule complex is formed. The target is exposed to potential ligands by various methods, including but not limited to, soaking a crystal in a solution of one or more potential ligands or co-crystallizing a biomolecule in the presence of one or more potential ligands.

In a further embodiment, structural information from the ligand/receptor complexes found are used to design new ligands that bind tighter, bind more specifically, have better biological activity or have better safety profile than known ligands.

In a preferred embodiment, libraries of "shape-diverse" compounds are used to allow direct identification of the ligand-receptor complex even when the ligand is exposed as part of a mixture. This avoids the need for time-consuming de-convolution of a hit from the mixture. Here, three important steps are achieved simultaneously. The calculated electron density function directly reveals the binding event, identifies the bound compound and provides a detailed 3-D structure of the ligand-receptor complex. In one embodiment, once a hit is found, one could screen a number of analogs or derivatives of the hit for tighter binding or better biological activity by traditional screening methods. Another embodiment uses the hit and information about structure of the target to develop analogs or derivatives with tighter binding or better biological activity. In yet another embodiment, the ligand-receptor complex is exposed to additional iterations of potential ligands so that two or more hits can be linked together to make a more potent ligand.

BRIEF DESCRIPTION OF THE DRAWINGS

FIG. 6A is the initial Fo-Fc map. FIG. 6B shows how the compound binds at the active site of urokinase. FIG. 6C illustrates the active site without a bound ligand when no compound of the mixture has bound.

FIG. 7A is the initial Fo-Fc map. FIG. 7B shows how the compound binds at the active site of urokinase.

FIG. 8A is the initial Fo-Fc map. FIG. 8B shows how the compound binds at the active site of urokinase.

FIG. 9A is the Fo-Fc map for a strong ligand within the mixture. FIG. 9B is the Fo-Fc map for a weaker ligand within the mixture. The weaker ligand was detected only after the strong ligand was removed from the mixture.

DETAILED DESCRIPTION OF THE INVENTION

Figure 1:
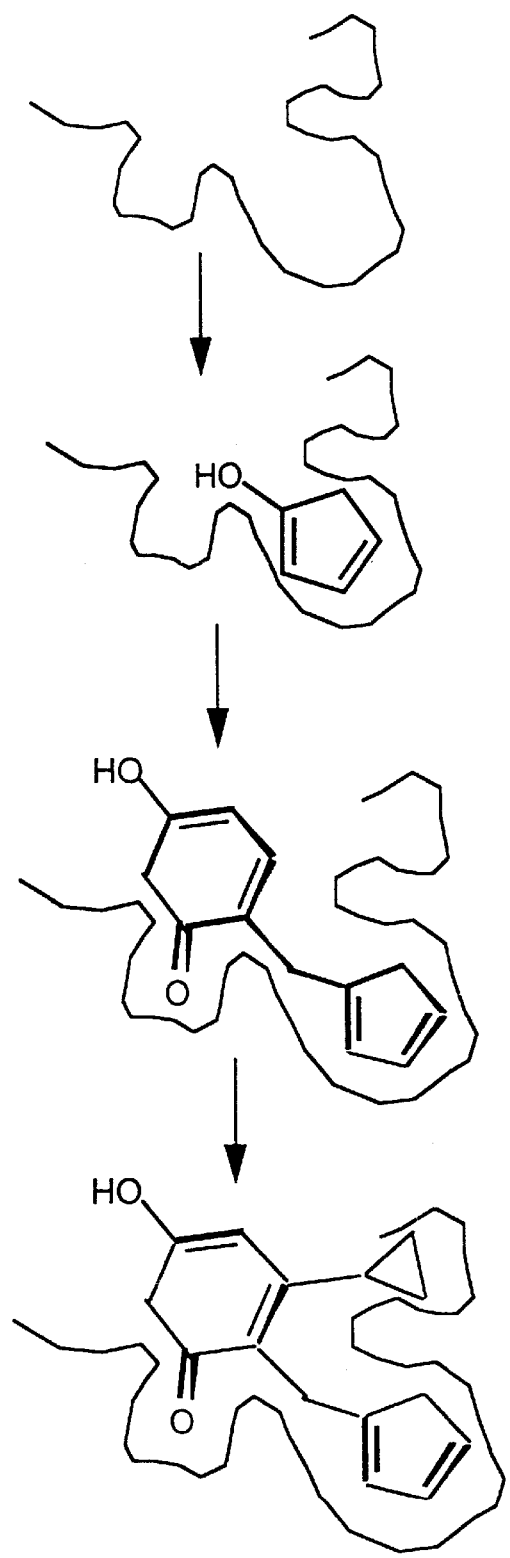
FIG. 1 illustrates a structure-based drug design where an initial lead compound is found, and then used as a scaffold to carry additional moieties that fit the subsites that surround a major site.

CrystaLEAD™ provides an efficient screening method for identifying compounds that will bind to a target biomolecule. Such compounds can serve as leads or scaffolds to design ligands and/or drugs that have improved biological activity for the target. One must note that tighter binding ligands do not necessarily provide better biological activity or make a better drug, although this is the general rule. It is possible for a weaker binding ligand to provide better biological activity due to factors other than tight binding (e.g., selectivity, bioavailability).

Crystallography has been used extensively to view receptor-ligand complexes for structure-based drug design. To view such complexes, known ligands are usually soaked into the target molecule crystal, followed by crystallography of the complex. Sometimes, it is necessary to co-crystallize the ligands with the target molecule to obtain a suitable crystal.

Until now, crystallography has not been implemented to screen potential ligands despite the detailed structural information that it provides. Possible prejudices against screening compounds by crystallography include the belief that the method is too complicated or time consuming, that suitable crystals are difficult to obtain, that available crystals could not tolerate soaking more than one compound (much less mixtures of ten or more compounds), that too much biomolecule would be needed, that it would be too time consuming to routinely mount crystals, and that constantly changing crystals on the x-ray goniometer would be too tedious.

However, currently available technology has overcome many of these perceived barriers. For example, at one time, molecular targets were only obtained from natural sources and were sometimes unsuitable for crystallization due to natural degradation or glycosylation. In addition, the natural concentration was often too low to obtain the amount of highly purified protein necessary for crystallization. With molecular biology, large amounts of protein may be expressed and purified for crystallization. When necessary, the protein can even be re-engineered to provide different or better crystal forms.

Further, brilliant light sources (synchrotron radiation) and more sensitive detectors have become readily available so that the time required to collect data has been reduced dramatically from days to hours or even minutes. Furthermore, existing technologies which are less routine at this time, but may become routine soon, allow full data set collections in the order of seconds or even fractions of a second (e.g., Laue diffraction). J. Hajdu et al., *Nature*, v. 329, pp. 178–81 (1987). Faster computers and more automation software have greatly decreased the time required for data collection and analysis. Finally, the inventors have discovered that it is possible to soak or co-crystallize mixtures of compounds to screen for potential ligands. Thus, as described below, crystallography is now a practical and feasible screening method.

In CrystaLEAD™, ligands for a target molecule having a crystalline form are identified by exposing a library of small molecules, either singly or in mixtures, to the target (e.g. protein, nucleic acid, etc.). Then, one obtains crystallographic data to compare the electron density map of the putative target-ligand complex with the electron density map of the target biomolecule. The electron density map simultaneously provides direct evidence of ligand binding, identification of the bound ligand, and the detailed 3-D structure of the ligand-target complex. Binding may also be monitored by changes in individual reflections within the crystallographic diffraction pattern which are known to be sensitive to ligand binding at the active site. This could serve as a pre-screen but would not be the primary method of choice because it provides less detailed structural information.

By observing changes in the level of ligand electron density or the intensity of certain reflections in the diffraction pattern as a function of ligand concentration either added to the crystal or in co-crystallization, one may also determine the binding affinities of ligands for biomolecules. Binding affinities may also be obtained by competition experiments. Here, the new compound(s) are soaked or co-crystallized with one of a series of diversely-shaped ligands of known binding affinity. If the known ligand appears in the electron density map, the unknown ligands are weaker binders. However, if one of the new compounds is found to compete for the site, it would be the tightest binder. By varying the concentration or identity of the known ligand, a binding constant for the CrystaLEAD™ hit may be estimated.

The number of compounds screened is based upon the desired detection limit, the compound solubility and the amount of organic co-solvent the crystals will tolerate. Exact numbers depend on each crystal. For example, for a typical crystal that tolerates 1% organic co-solvent, the sensitivity limit would be Kd<1.5 mM to screen 10 compounds simultaneously. For 20 compounds, the sensitivity limit would be Kd<0.63 mM. However, crystals that tolerate high organic co-solvents (e.g., 40%), can screen up to 50 compounds within a detection limit of Kd<1.5 mM.

In the most general application of CrystaLEAD™, the hit or lead compound is used to determine what compounds should be tested for biological activity in structure-based drug design. Then derivatives and analogs are obtained by traditional medicinal chemistry to find the best ligand or drug.

Alternatively, the structural information collected in the screening process can be used directly to suggest analogs or derivatives of the hit. This approach is illustrated when the active site is composed of one primary pocket surrounded by a variety of subsites and small pockets (FIG. 1). Detailed structural information about how a compound is bound by the receptor is obtained simultaneously as a hit is detected. Such information is useful to the ordinary artisan for designing better ligands. P. Colman, *Curr. Opin. in Struct. Biology*, v. 4, pp. 868–74 (1994); J. Greer et al., *J. Med. Chem.*, v. 37, pp. 1035–54 (1994); C. Verlinde et al., *Structure*, v. 15, pp. 577–87 (1994). In particular, the hit identifies sites for analog synthesis which would permit access to the surrounding subsites and small pockets. This suggests the design of new compounds which better fit the active site. Furthermore, in cases where there is an existing structure-function relationship, activity enhancing substitution patterns may be directly transferred to the new lead scaffold at the 3-D structural level.

Figure 2:
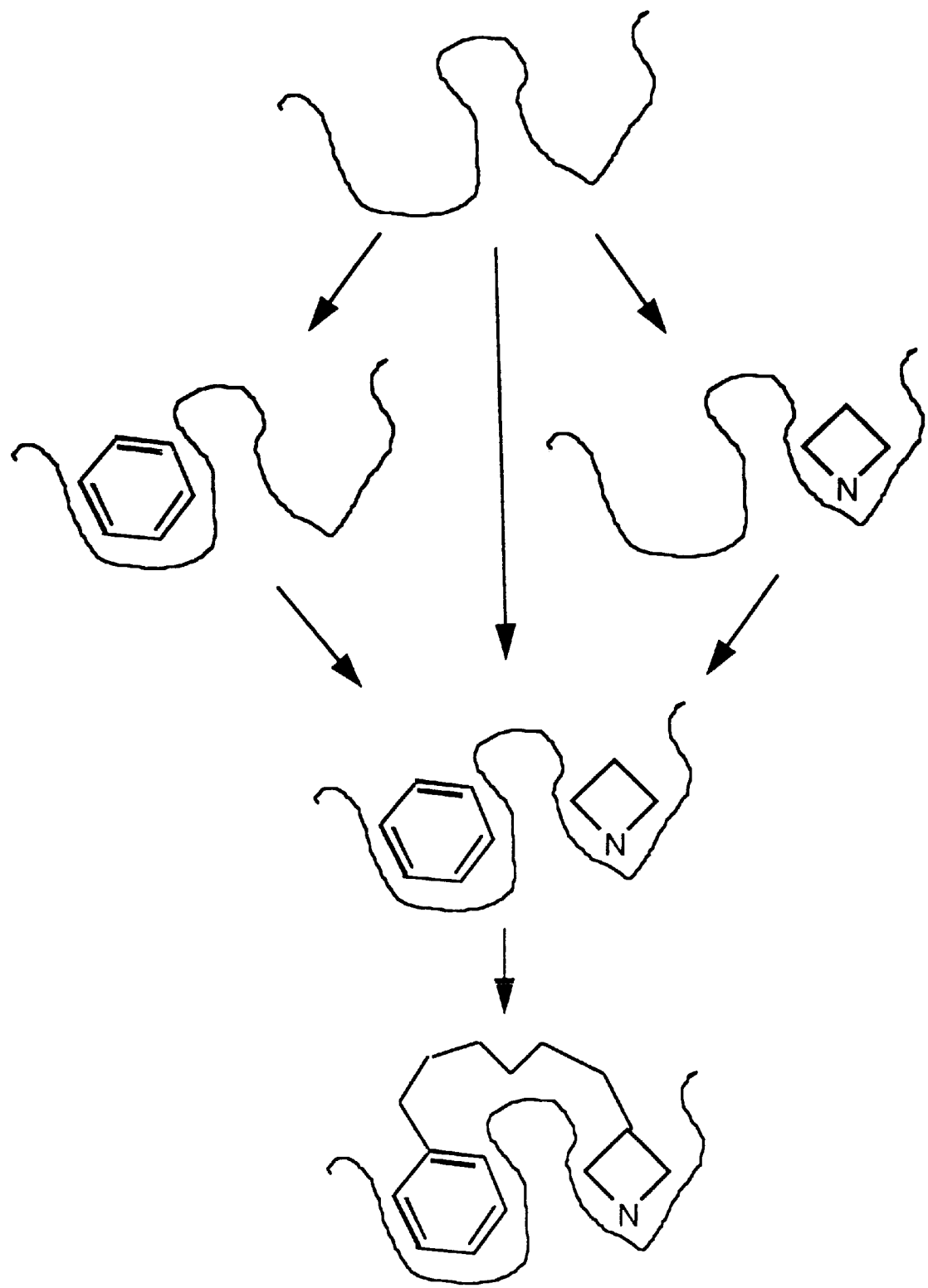
FIG. 2 illustrates a fragment linking approach for a biomolecule having two or more adjacent primary pockets.

Another illustration (FIG. 2) usually applies to a target that has two or more separate pockets that will accommodate fragments. Here, the crystalline target is screened for ligands that occupy all of the sites either in sequence or simultaneously. Because the binding event is monitored by visualizing co-crystal structures, the site of ligand binding is identified directly and there is no need for competition experiments to assure that the ligands indeed occupy different sites on the protein. Screening separately allows for ligands which bind to distinct pockets that overlap in their binding loci. Screening for the second in the presence of the first would detect cooperative binding at a second site. Once potential leads and a structure-activity relationship have been established, linkages between each of the sites may be designed using the detailed structural information and the fragment linking approach as previously described to produce novel, much more potent ligands. S. B. Shuker et al., *Science*, v. 274, pp. 1531–34 (1996); C. Verlinde et al., *Structure*, v. 15, pp. 577–87 (1994).

In a third application, the scaffold merging approach (not shown), the target active site is composed of two or more subsites. The crystalline protein is screened for ligand/s which bind via these subsites and the relative ligand binding orientation observed for multiple experiments. These ligands should bind by occupying one or more subsites and by overlaying the structures of multiple hits a core may be designed that will facilitate access to multiple subsites. This core would then serve as a new, novel and more potent lead compound which would also serve as the lead scaffold in the drug-design cycle.

The CrystaLEAD™ linked-fragment approach experimentally implements the structure-based linked-fragment approach reported only at the computational level by Verlinde et al. in *J. Comput. Aided Mol. Des.*, v. 6, pp. 131–47 (1992). Verlinde et al. proposed ligand fragments based on mathematical calculations. The proposed fragments were then assayed for binding activity. If the fragments actually bound, their 3-D structures were determined by X-ray crystallography and a linker designed. By contrast, CrystaLEAD™ concurrently detects the binding event and provides an experimentally determined 3-D structure of the ligand-protein complex. The invention also provides for a process of determining the association constant between a target molecule and its ligand. The invention requires no special labeling of the target. Therefore, the target molecule, can encompass proteins, polypeptides, nucleic acids, nucleoproteins, or any other suitable target molecule, that is isolated from natural sources or by recombinant methods from any suitable host system as developed and practiced by the ordinary artisan.

There are several advantages to crystallographic screening. One important advantage is that the binding event is monitored directly so that the probability for false positives is reduced to near zero. The crystallographic data provide a three dimensional electron density "snap-shot" of the ligand-receptor complex showing which compound binds and how it is bound.

The method is uniquely sensitive to structural changes in both the target and the ligand. Observing structural changes is critical in designing scaffolds which combine information from different ligand-target complex structures. One such example occurs when a protein changes structure in order to accommodate one ligand, but the structure change concurrently blocks the binding of a second ligand. Similarly, detecting structural changes is also important because if the primary scaffolds bind differently, it may not be possible to combine them into a larger scaffold.

Since the binding event is monitored directly, CrystaLEAD™ does not require specially labeled samples, probes or target molecules which would be indirectly sensitive to ligand association. As long as one is able to obtain a crystal structure of the target, one can use CrystaLEAD™ to screen for ligands.

If compound mixtures are suitably designed to be shape-diverse, the invention alleviates the need for de-convolution of libraries which are soaked as a mixture because the binding event is detected directly by examining the shape of the electron density at the binding site. Thus, the shape of the electron density identifies both the binding event and the compound identity directly. Alternatively, one can design the mixture to contain compounds with anomalous scattering atoms (e.g. Br, S) that can be identified by anomalous scattering techniques. Further, because CrystaLEAD™ directly monitors binding, it is particularly well-suited for studying targets where no known ligand exist.

Because the electron density function calculated in CrystaLEAD™ shows the "real space" of the crystal, one can focus directly on the region of interest. Thus, binding may be detected exclusively at the site of interest although the method is not limited to the active site. Binding at other sites, which complicates analysis in most binding assays, can be eliminated from consideration totally.

CrystaLEAD™ also provides for a method of concurrently monitoring binding at different locations. That is, for a target with more than one pocket, screening for a second site does not require screening in the presence of the first ligand. However, screening for a second site may be completed in the presence of the first ligand in order to discover cooperative ligands.

CrystaLEAD™ is applicable for any target molecule for which a crystal structure can be obtained. According to current literature, this includes any soluble macromolecule with molecular weight between about 5000 and 200,000. However, this range expands almost daily in response to technological advances. The method is also sensitive to a wide range of binding dissociation constants (<picomolar to molar). Using more sensitive CCD camera detectors, data may be collected in about <4 hrs to about 4 hours with a rotating anode source. This permits the screening of thousands of compounds per detector per day. Using synchrotron sources, the number of compounds screened increase to multiple thousands per detector, and with Laue data collection methods and testing mixtures, CrystaLEAD™ data can be collected in a second or less, thus permitting thousands of compounds to be tested per day per beamline. Hence, multiple detectors or a single synchrotron beamline facilitates true high-throughput screening.

Figure 3:
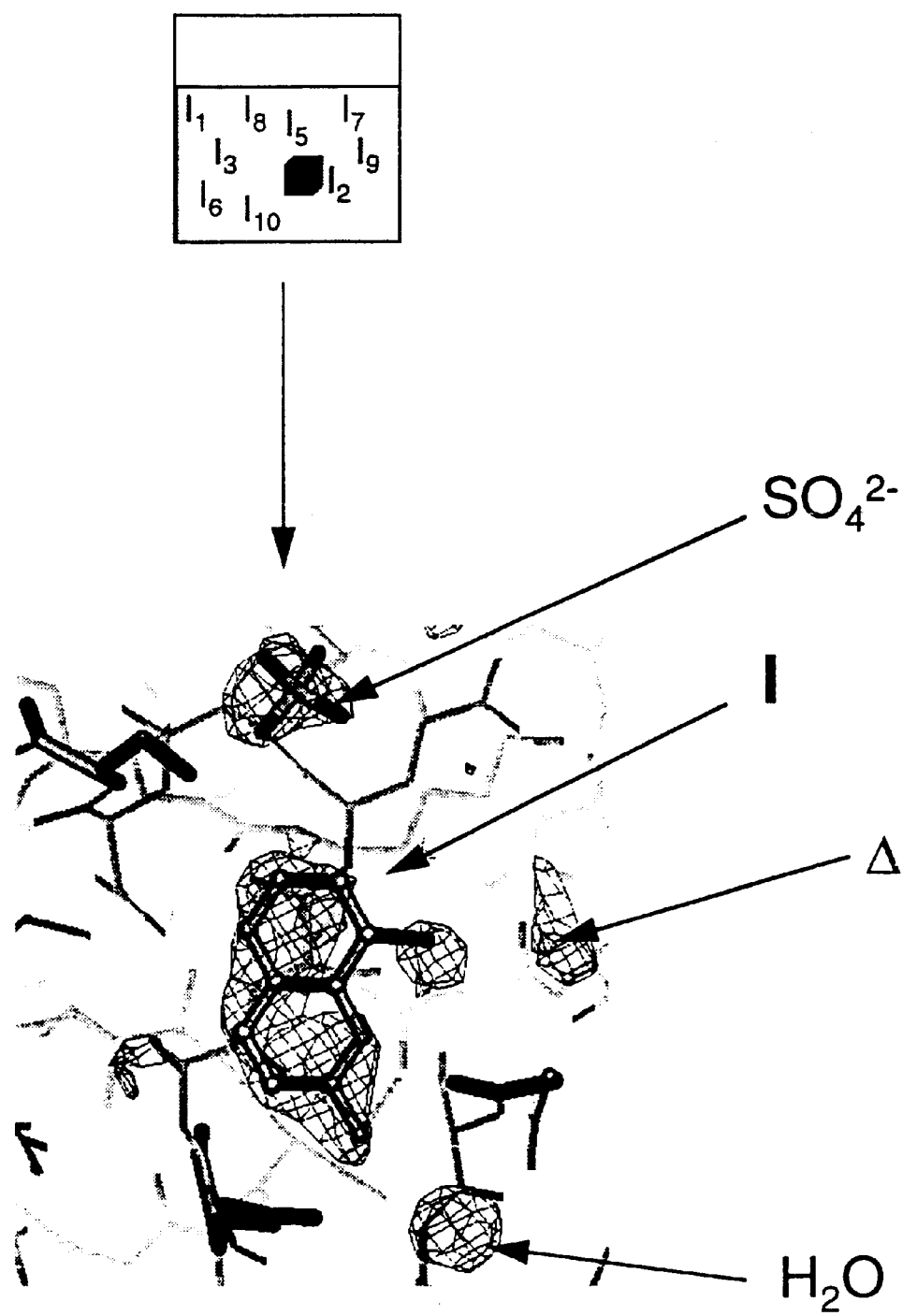
FIG. 3 is an outline of CrystaLEAD™ wherein a crystal is soaked in a solution of various potential ligands ($I_1$–$I_{10}$) and an X-ray diffraction dataset is collected and transformed into an electron density map which is inspected for compound binding.

FIG. 3 outlines the invention. Crystals of the target molecule are exposed to one or more compounds by soaking the crystal or by co-crystallizing the target in the presence of one or more compounds. Then crystallographic data are collected, processed and converted to electron density maps which are examined for evidence of ligand binding. One way to detect ligand binding is to compare the structure of the original crystal with the structure of the exposed crystal.

New targets may be crystallized by published conditions or by other methods well established in the art. Similarly, target structures may be available from databases such as the Protein Data Bank or could be determined by well established methodology. Advances in molecular biology and protein engineering expedite target crystallization while advances in data collection aid in rapid structure determination for targets of previously unknown structure.

Crystals that are exposed to potential ligands by soaking require an empty accessible active site. Crystals with an empty active site may be obtained by various methods, including but not limited to: crystallization in the absence of a ligand; crystallization in the presence of ligand bound at a distal site; or crystallization in the presence of a non-covalent ligand that is easily diluted or exchanged from the target once the biomolecule crystallizes. By a novel method, the inventors have obtained crystals from a biomolecule by crystallizing the biomolecule in the presence of a degradable ligand at the active site and then degrading the ligand once a crystal is formed. Alternatively, it is possible to grow the crystals in the presence of the compounds to be screened. Crystals are allowed to equilibrate in the presence of the mixture, at which point the ligands bind as a function of their concentration and binding affinity.

For the soaking method, the sensitivity of the method may be approximated by simple equilibria relationships because the concentration of protein in the crystal may be calculated and the concentration of ligand is a known quantity. For example, the concentration of a 25,000 MW protein (urokinase) in a crystal is calculated as follows: there are 4 molecules in the orthorhombic unit cell (all angles 90°) which has a volume of 55×53×82 $Å^3$; using Avogadro's number, the concentration is 28 mM. Therefore, a mixture of compounds having a 6 mM concentration for each ligand will result in a calculated sensitivity limit of Kd<1.5 mM (assuming a detection limit of about 80% occupancy in the crystal).

Soaking mixtures of compounds also raises the question of multiple occupancy (more than one ligand binding to the site of interest). For cases of multiple occupancy where the ligands are bound in different pockets (see FIG. 2), resolution by CrystaLEAD™ is easy because the binding at the separate sites can be distinguished individually by the electron density maps. For the scenario where different ligands compete to occupy the same site, one may use a simple competitive inhibition model to calculate the requirements for such binding. From empirical observation, it is believed that crystallography can resolve situations where the occupancy of one inhibitor is 80% and another 20%. Therefore, a ratio of binding affinity that is greater than four would result in an apparent occupancy by only the higher-affinity ligand. In the unlikely case where the ratio of binding constants of two compounds in the mixture are less than four, the resulting electron density would be a weighted average of the two separate densities and might be difficult to identify. Accordingly, it would be necessary to conduct further soaking experiments to de-convolute the mixture (e.g., looking at each compound individually in separate crystals) only where the ratio of binding affinities is less than four. This would still be worthwhile and efficient because it already determines that at least two hits are present in the mixture.

Compounds to be screened are formed into libraries. For the purposes of this discussion, libraries are large mixtures of compounds (100–10,000+) and may be general or structure-directed. A general library is random, i.e. fully diverse in size, shape and functionality. A structure-directed library is aimed at a particular functional mixture or subsite in the active site of the target molecule (e.g., a library where all compounds contain a carboxylate functionality to be directed towards a positive charge in the target active site).

Figure 4:
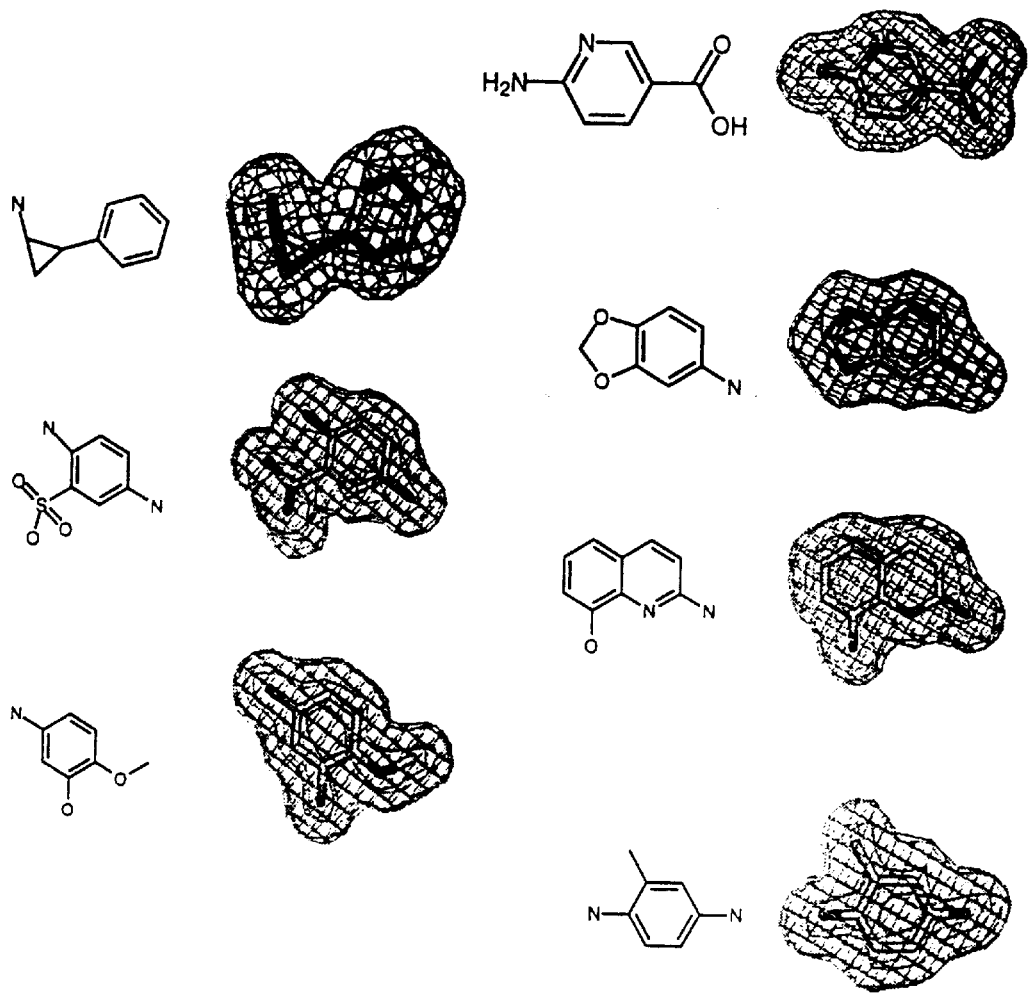
FIG. 4 illustrates a typical compound mixture in 2-D and 3-D. The 3-D figures are theoretical 2Fo-Fc electron density maps that represent the "shape" of the molecules.

In a preferred embodiment, either type of library is divided into smaller groups of shape diverse mixtures. Hence, a mixture is defined as a subset of the library which may be soaked or grown into the crystal. The mixture is determined to be shape diverse by visual inspection of the two dimensional chemical structures or computationally by programs. Shape diversity of the mixture permits a bound ligand to be identified directly from the resultant electron density map (see FIG. 4). This eliminates the need for follow-up experiments to determine which compound of the mixture is a hit (bound to the target).

If the test compounds are water soluble, typical buffers and precipitant solutions used in crystallization can be used to solubilize the mixtures and soak them into the crystal. Less water soluble compounds are dissolved individually to a final concentration of 2M in a suitable organic solvent. In one embodiment, they are dissolved in 100% DMSO and stored at 4° C., and mixed by mixing the DMSO stocks before exposure to the crystal. These mixtures would service most crystal systems where the conditions for crystal growth do not include organic reagents. The compounds would be typically soaked to a final DMSO concentration of 1–10% and allowed to equilibrate with the crystalline protein for a pre-determined amount of time (4–24 hrs). Under this scenario, each crystal is exposed to multiple compounds per soaking mixture. Some crystal growth conditions can include a high concentration of organic solvent (40–50%) which are typically alcohol derivatives. In this case, the compound libraries may be dissolved in the crystallization organic solvent which would allow a final co-solvent concentration of 40–50% for the soaking experiment. Here, the number of compounds per soaking mixture could increase.

After soaking, each crystal is exposed to a cryoprotectant such as 5–20% glycerol in the soaking mixture, mounted in a nylon loop and placed on the X-ray unit under a nitrogen cold stream (160K). The crystal studies may also be performed at room temperature or other suitable conditions as necessary for the stability of the crystals. Automated crystal mounting and changing equipment may be used to accelerate this step of the process.

Crystallographic data are collected and processed where each reflection (spot) on the diffraction pattern is assigned an index (h,k,l) and the intensity is measured as standard in the field. X-ray sources may be laboratory x-ray generators or high brilliance synchrotron sources that permit diffraction data collection at very high speed. Specifically, laboratory data collection may take from 30 minutes to several hours per crystal while the time can be reduced using synchrotron sources. Data collection per crystal could be reduced to fractions of a second using Laue data collection schemes.

The diffraction data are then converted to electron density maps by methods familiar to the ordinary artisan. The electron density maps are the 3-D pictures of the ligands and/or the target biomolecules.

For Fo-Fc maps, the calculated structure-factor amplitudes (|Fc|) which are obtained from the known crystal structure with no ligand bound are subtracted from the observed amplitudes (|Fo|). Thus, this map represents a direct subtraction of the data arising from the native protein structure from data arising from crystals soaked in the presence of a library mixture. The result is an electron density map which has positive and negative peaks. The peaks relevant to CrystaLEAD™ are the positive ones which are the direct result of ligand binding at the site of interest on the target—that is the addition of the ligand into the target biomolecule. In FIG. 3, the Fo-Fc map clearly shows a large positive peak at the active site of urokinase. The shape of the peak corresponds to the ligand 2-amino-8-hydroxyquinoline. The ligand is shown occupying the positive difference density. The other positive peaks correspond to a bound sulfate moiety (indicated by $SO_4^{2-}$) and bound water molecules (indicated by $H_2O$). This type of map is also very sensitive to small structural changes (indicated by Δ) that, when used in conjunction with 2Fo-Fc maps, allows determination of the detailed structure of the entire ligand-protein complex. To calculate the 2Fo-Fc maps, one subtracts (|Fc|) from 2(|Fo|). Here, the map is positive and has density for all atoms of the molecule.

In FIG. 3, inspection of the map indicates the identity and structure of the bound compound. Preferably, the maps of exposed crystals are compared with the maps of the unexposed target molecule to differentiate the positive density that may be found in the Fo-Fc map. Sometimes water molecules occupy the active site in the crystal in the absence of a bound ligand. This is easily differentiated because bound water molecules are often oriented in a geometry consistent with hydrogen bonding and because they are not connected by a network of covalent bonds. Thus, the resultant map tends to be disconnected indicating bound solvent rather than an organic compound. If the density in the Fo-Fc or 2Fo-Fc map is determined to represent an organic compound, the three-dimensional shape is compared to that of the compounds present in the library and a bestfit match is made. Alternatively, programs such as the XFIT modules of QUANTA (Molecular Simulations Inc., Quanta Generating and Displaying Molecules, San Diego: Molecular Simulations Inc., 1997) can automate this process.

As the ability to measure or process diffraction intensities improves, one may not need to perform the comparison on electron density maps. One may detect binding by simply comparing the diffraction patterns of the exposed crystals with the unexposed crystals. Therefore, one needs to create an electron density map only if a binding event is detected in this pre-screening process.

As shown above, CrystaLEAD™ can be applied to any biomolecular target for which a crystallographic structure can be obtained. Because of its broad applicability, it is best illustrated by the examples below.

The urokinase and VanX examples represent two scenarios for the use of CrystaLEAD™. For urokinase, the re-engineered microUK (μUK) crystals diffract very well and are of a high symmetry space group. By contrast, VanX crystals diffract more weakly and with lower symmetry. Thus, VanX requires greater data collection time. In addition, urokinase crystals have one molecule in the asymmetric unit, while VanX has six. The larger asymmetric unit requires collection of higher resolution data and makes map inspection more tedious. However, in the case of VanX, no non-substrate mimetic binders were known before those discovered by CrystaLEAD™. Therefore, CrystaLEAD™ provided a novel non-peptidic lead compound to be fed into the drug-discovery cycle. For urokinase, CrystaLEAD™ provided a novel primary scaffold. Applicants were able to rapidly increase the potency of the primary scaffold by using existing SAR and crystal structures to design a higher-affinity derivative with improved bioavailability over known urokinase ligands.

However, these examples illustrate the preferred embodiment of the present invention, and do not limit the claims or the specification. The ordinary artisan will readily appreciate that changes and modifications to the specified embodiments can be made without departing from the scope and spirit of the invention. Finally, all citations herein are incorporated by reference.

EXAMPLES

Example 1

Urokinase

Urokinase, a serine protease, is strongly associated with tumor cells. Urokinase activates plasminogen into plasmin which, in turn, activates the matrix metalloproteases. Plasmin and the metalloproteases degrade the extracellular matrix and promote tumor growth and metastasis. Thus, inhibitors that specifically target urokinase may serve as effective anti-cancer agents.

Figure 5:
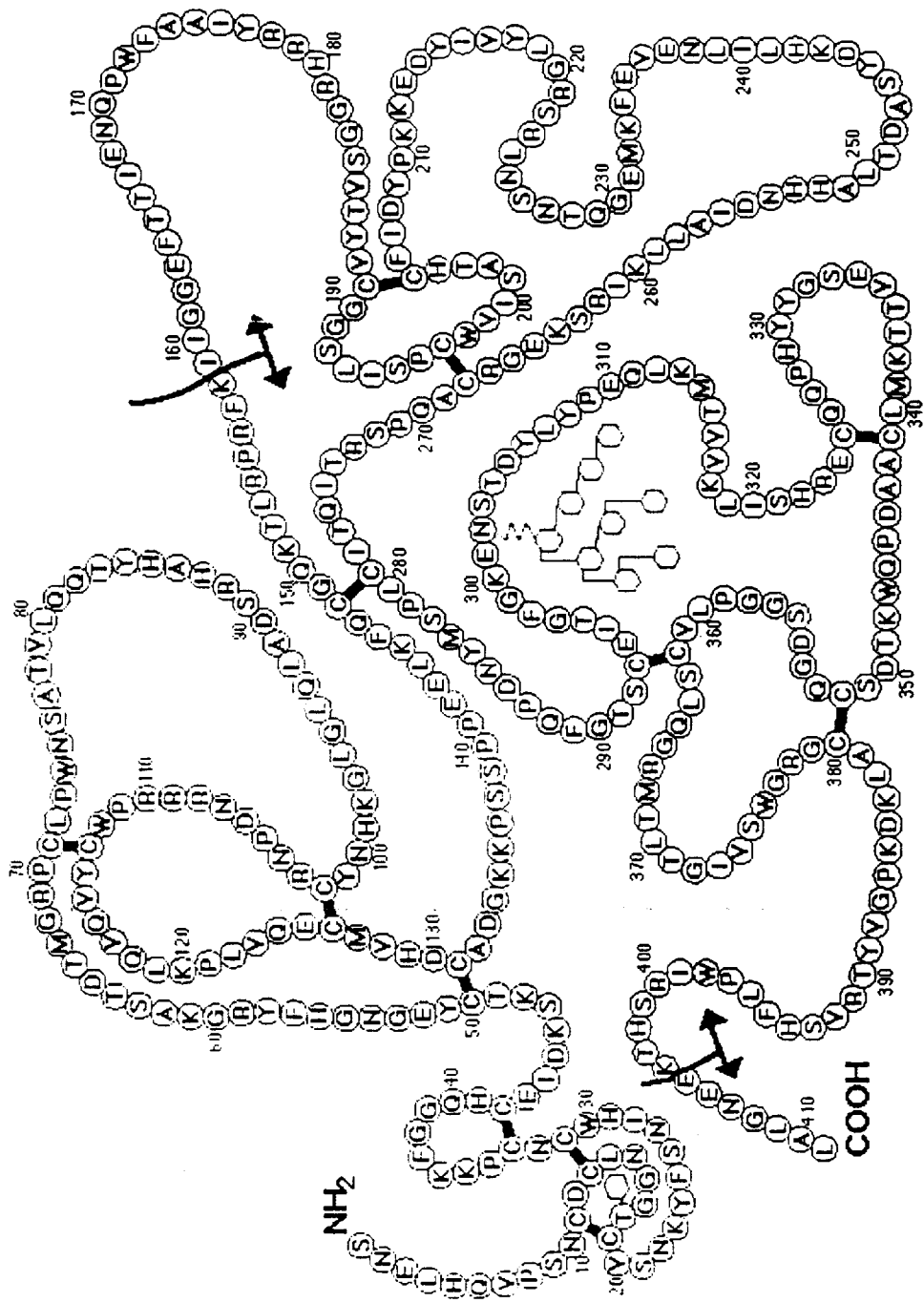
FIG. 5 is a primary sequence of human urokinase.

Human pro-urokinase consists of 411 amino acids (FIG. 5). Verde et al., Proc. Nat'l Acad. Sci., v. 81(5), pp. 4727–31 (1984); Nagai et al., Gene, v. 36(1–2), pp. 183–8 (1985). When activated by proteolytic cleavage at the $Lys^{158}$-$Ile^{159}$ peptide bond, the enzyme becomes two chains connected by a single disulfide bridge ($Cys^{148}$-$Cys^{279}$). The A-chain (residues 1–158) contains an EGF-like domain and a kringle domain. The B-chain (residues 159–411) contains the catalytic serine protease domain. Further incubation of urokinase results in an additional proteolytic cleavage at the $Lys^{135}$-$Lys^{136}$ peptide bond to form low-molecular-weight urokinase. Crystals of this enzyme form in complex with the covalent inhibitor Glu-Gly-Arg chloromethyl ketone were obtained by Spraggon et al., Structure, v. 3, pp. 681–91 (1995), and were shown to diffract to 2.5 Å resolution at a high energy synchrotron source. However, the poor diffraction quality of these crystals together with the presence of a covalently bound inhibitor makes application of CrystaLEAD™ difficult.

μUK Crystal Preparation & Structure

To implement CrystaLEAD™, human urokinase was re-engineered to consist only of residues 159–404 of the B-chain where $Asn^{302}$ was replaced with a glutamine to remove a glycosylation site and $Cys^{279}$ was replaced with an alanine to remove the free sulfhydryl moiety. This form of urokinase (μUK) was shown to be fully active and was found to crystallize in a crystal form compatible with CrystaLEAD™. (See, also, U.S. Pat. No. 5,112,755, issued May 12, 1992, to Heyneker et al.)

Preparing Vector Construct pBC-LMW-UK-$Ala^{279}$

Mutants of human UK were cloned into a dicistronic bacterial expression vector pBCFK12. Pilot-Matias et al., Gene, v. 128, pp. 219–25 (1993). The following oligo nucleotides were used to generate various UK mutants by PCR:

| SEQ ID # | SEQUENCE OF PCR PRIMER |
|---|---|
| 1 | 5'-ATTAATGTCGACTAAGGAGGTGATCTAATGTTAAAATTTCAGTGTGGCCAA-3' |
| 2 | 5'-ATTAATAAGCTTTCAGAGGGCCAGGCCATTCTCTTCCTTGGTGTGACTCCTGATCCA-3' |
| 3 | 5'-ATTAATTGCGCAGCCATCCCGGACTATACAGACCATCGCCCTGCCCT-3' |

The initial cloning of a low molecular weight UK, hereinafter designated LMW-UK ($L^{144}$–$L^{411}$) was performed using human UK cDNA as template and SEQ ID NOs: 1 and 2 as primers in a standard PCR reaction. The PCR amplified DNA was gel purified and digested with restriction enzymes SalI and HindIII. The digested product then was ligated into a pBCFK12 vector previously cut with the same two enzymes to generate expression vector pBC-LMW-UK. The vector was transformed in DH5α cells (Life Technologies, Gaithersburg, Md.), isolated and the sequence confirmed by DNA sequencing. The production of LMW-UK in bacteria was analyzed by SDS-PAGE and zymography, Granelli-Piperno et al., *J. Exp. Med.*, v. 148, pp. 223–34 (1978), which measures plasminogen activation by UK. That LMW-UK was expressed in *E. coli*, and that it was active in the zymographic assay was demonstrated by commassie blue stained gel.

The success of the quick expression and detection of LMW-UK in *E. coli* made it possible to perform mutagenesis analysis of UK in order to determine its minimum functional structure. One mutant having a $Cys^{279}$ to $Ala^{279}$ replacement was made with SEQ ID Nos: 2 and 3 by PCR. The PCR product was cut with AviII and Hind III, and used to replace a AviII and Hind III fragment in the pBC-LMW-UK construct. The resulting pBC-LMW-UK-$Ala^{279}$ construct was expressed in *E. coli* and the product shown to be active in zymography.

Cloning and Expressing $\mu$UK (UK($I^{159}$-$K^{404}$)$A^{279}Q^{302}$) in Baculovirus $\mu$UK (UK amino acids $Ile^{59}$-$Lys^{404}$ that contain $Ala^{279}Gln^{302}$) was generated by PCR with the following oligonucleotide primers:

*Virology*, v. 64(1); pp. 37–50, (1990). The resulting construct, pJVP10z-$\mu$UK was confirmed by standard DNA sequencing techniques.

Construct pJVP10z-$\mu$UK was transfected to Sf9 cells by the calcium phosphate precipitation method using the BaculoGold kit from PharMingen (San Diego, Calif.). Active $\mu$UK activity was detected in the culture medium. Single recombinant virus expressing $\mu$UK was plaque purified by standard methods, and large stock of the virus was made.

Large scale expression of $\mu$UK was made in another line of insect cells, High-Five cells (Invitrogen, Carlsbad, Calif.), in suspension growing in Excel 405 serum-free medium (JRH Biosciences, LeneXa, Kans.) in 2 liter flasks, shaking at 80 rpm, 28° C. High-Five cells own to $2\times10^6$ cells/ml, recombinant $\mu$UK virus was added at 0.1 multiplicity of infection, and the culture was continued for 3 days. The culture supernatant was harvested as the starting material for purification. The activity of $\mu$UK in the culture supernatant was measured by amidolysis of a chromogenic UK substrate S2444, which was at 6–10 mg/liter. Claeson et al., *Haemostasis*, v. 7, p. 76 (1978).

Expressing $\mu$UK in Pichia Pastoris

To express $\mu$UK in Pichia, an expression vector with a synthetic leader sequence was used. The Pichia expression vector, pHil-D8, was constructed by modifying vector pHil-D2 (Invitrogen) to include a synthetic leader sequence for secretion of a recombinant protein. The leader sequence 5'-ATGTTCTCTCCAATTTTGTCCTTGG AAATTATTTTAGCTTTGGCTACTTTGCAAT CTGTCTTCGCTCAGCCAGTTATCTGCACTACCGTTG GTTCCGCTGCCGAGG GATCC-3' (SEQ ID NO: 10)

| SEQ ID # | SEQUENCE OF PCR PRIMER |
|---|---|
| 4 | 5'-ATTAATCAGCTGCTCCGGATAGAGATAGTCGGTAGACTGCTCTTTT-3' |
| 5 | 5'-ATTAATCAGCTGAAAATGACTGTTGTGA-3' |
| 6 | 5'-ATTAATGTCGACTAAGGAGGTGATCTAATGTTAAAATTTCAGTGTGGCCAA-3' |
| 7 | 5'-ATTAATGCTAGCCTCGAGCCACCATGAGAGCCCTGCT-3' |
| 8 | 5'-ATTAATGCTAGCCTCGAGTCACTTGTTGTGACTGCGGATCCA-3' |
| 9 | 5'-GGTGGTGAATTCTCCCCCAATAATGCCTTTGGAGTCGCTCACGA-3' |

To mutate the only glycosylation site ($Asn^{302}$) in UK, oligonucleotide primers SEQ ID NOs: 4 and 6, and SEQ ID NOs: 5 and 8 were used in two PCR reactions with pBC-LMW-UK-$Ala^{279}$ as the template. The two PCR products were cut with restriction enzyme Pvu II, ligated with T4 DNA ligase, and used as template to generate LMW-UK-$A^{279}$-$Q^{302}$. In the meantime, native UK leader sequence was fused directly to $Ile^{159}$ by PCR with SEQ ID NOs: 7 and 9 using native UK cDNA as the template.

This PCR product was used as a primer, together with SEQ ID NO: 8, in a new PCR reaction with LMW-UK-$A^{279}$-$Q^{302}$ DNA as template to generate $\mu$UK cDNA. $\mu$UK was cut with Nhe I and ligated to a baculovirus transfer vector pJVP10z cut with the same enzyme. Vialard et al, *J.* encodes a $PHO_1$ secretion signal (indicated by the single underline) operatively linked to a pro-peptide sequence (indicated in bold) for KEX2 cleavage. To construct pHil-D8, PCR was performed using pHil-S1 (Invitrogen) as template since this vector contains the sequence encoding PHO1, a forward primer (SEQ ID NO: 11) corresponding to nucleotides 509–530 of pHil-S1 and a reverse primer (SEQ ID NO: 12) having a nucleotide sequence which encodes the latter portion of the PHO1 secretion signal (nucleotides 45–66 of SEQ ID NO: 10) and the pro-peptide sequence (nucleotides 67–108 of SEQ ID NO: 10). The primer sequences (obtained from Operon Technologies, Inc. Alameda, Calif.) were as follows:

| SEQ ID | #SEQUENCE OF PCR PRIMER |
|---|---|
| 11 | 5'-GAAACTTCCAAAAGTCGCCATA-3' |
| 12 | 5'-ATTAATGAATTCCTCGAGCGGTCCGGGATCCCTCGGCAGCGGAACCAACGGTAGTGCAG ATAACTGGCTGAGCGAAGACAGATTGCAAAGTA-3' |

Amplification was performed under standard PCR conditions. The PCR product (approximately 500 bp) was gel-purified, cut with BlpI and EcoRI and ligated to pHil-D2 cut with the same enzymes. The DNA was transformed into E. coli HB101 cells and positive clones identified by restriction enzyme digestion and sequence analysis. One clone having the proper sequence was designated as pHil-D8.

The following two oligonucleotide primers then were used to amplify μUK for cloning into pHil-D8.

| SEQ ID | #SEQUENCE OF PCR PRIMER |
|---|---|
| 13 | 5'-ATTAATGGATCCTTGGACAAGAGGATTATTGGGGGAGAATTCACCA-3' |
| 14 | 5'-ATTAATCTCGAGCGGTCCGTCACTTGGTGTGACTGCGAATCCAGGGT-3' |

The PCR product was obtained with SEQ ID NOs: 13 and 14 using pJVP10z-μUK as the template. The amplified product was cut with BamHI and XhoI and ligated to pHil-D8 cut with the same two enzymes. The resulting plasmid, pHilD8-μUK, was confirmed by DNA sequencing, and used to transform a Pichia strain GS115 (Invitrogen) according to the supplier's instructions. Transformed Pichia colonies were screened for μUK expression by growing in BMGY medium and expressing in BMMY medium as detailed by the supplier (Invitrogen). The μUK activity was measured with chromogenic substrate S2444. The μUK expression level in Pichia was higher than that seen in baculovirus-High Five cells, ranging from 30–60 mg/L.

Purifying μUK

The culture supernant of either High Five cells or Pichia were pooled into a 20 liter container. Protease inhibitors, iodoacetamide, benzamidine and EDTA were added to a final concentration of about 10 mM, 5 mM and 1 mM, respectively. The supernatant was then diluted 5-fold by adding 5 mM Hepes buffer pH7.5 and put through 1.2μ and 0.2 μ filter membranes. The μUK was captured onto Sartorius membrane adsorber S100 (Sartorius, Edgewood, N.Y.) by passing through the membrane at a flow rate of 50–100 ml/min. After extensive washing with 10 mM Hepes buffer, pH7.5, 10 mM iodoacetamide, 5 mM benzamidine, 1 mM EDTA, μUK was eluted from S100 membrane with a NaCl gradient (20 mM to 500 mM, 200 ml) in 10 mM Hepes buffer, pH7.5, 10 mM iodoacetamide, 5 mM benzamidine, 1 mM EDTA. The eluate (~100 ml) was diluted 10 times in 10 mM Hepes buffer containing inhibitors, and loaded to a S20 column (BioRad, Hercules, Calif.). μUK was eluted with a 20x column volume NaCl gradient (20 mM to 500 mM). No inhibitors were used in the elution buffers. The eluate was then diluted 5-fold with 10 mM Hepes buffer, pH7.5, and loaded to a heparin-agarose (Sigma) column. μUK was eluted with a NaCl gradient from 10 mM to 250 mM. The heparin column eluate of μUK (~50 ml) was applied to a benzamidine-agarose (Sigma, St. Louis, Mo.) column (40 ml) equilibrated with 10 mM Hepes buffer, pH7.5, 200 mM NaCl. The column was then washed with the equilibration buffer and eluted with 50 mM NaOAc, pH 4.5, 500 mM NaCl. The μUK eluate (~30 ml) was concentrated to 4 ml by ultrafiltration and applied to a Sephadex G-75 column (2.5×48 cm; Pharmacia® Biotech, Uppsala, Sweden) equilibrated with 20 mM NaOAc, pH4.5, 100 mM NaCl. The single major peak containing μUK was collected and lyophilized as the final product. The purified material appeared on SDS-PAGE as a single major band.

High-quality μUK crystals facilitated determination of its apo-three-dimensional structure by X-ray crystallography to 1.0 Å resolution. Crystals were obtained by the hanging drop vapor diffusion method. Typical well solutions consisted of 0.15M $Li_2SO_4$, 20% polyethylene glycol MW 4000 and succinate buffer pH 4.8–6.0. On the cover slip, 2 μl of well solution were mixed with 2 μl of protein solution and the slip sealed over the well. Crystallization occurred at approximately 18–24° C. within 24 hrs. The protein solution contained 6 mg/ml (0.214 mM) μUK in 10 mM citrate pH 4.0, 3 mM ε-amino caproic acid p-carbethoxyphenyl ester chloride (inhibitor) with 1% DMSO co-solvent. The inhibitor utilized in the co-crystallization is believed to acylate the active site serine 195 and is subsequently deacylated enzymatically, because, the 3-D X-ray structure of crystals grown in the presence of this compound show no inhibitor remaining in the enzyme active site. Menegatti et al., J. Enzyme Inhibition, v. 2, pp. 249–59 (1989). The only density present is that due to bound solvent molecules. Because μUK will not crystallize in the absence of the inhibitor, the meta-stable inhibitor:UK complex is believed to be the crystallization entity. Importantly, the resultant μUK crystals are composed of enzyme with an empty active site which is the ideal case for implementation of CrystaLEAD™.

Crystals obtained under these conditions belong to the space group $P2_12_12_1$ with unit cell dimensions of a=55.16 Å b=53.00 Å c=82.30 Å and α=β=γ=90°. They diffract to beyond 1.5 Å on a rotating anode source. Further, a 1.0 Å resolution native data set has been collected at the Cornell High Energy Synchrotron Source in Ithaca, N.Y. The crystal structure was determined by the molecular replacement method using the AMORE program, Navaza, J. Acta Cryst., A50:157–163 (1994), with the low-resolution urokinase structure as the search probe, Spraggon et al., Structure, v. 3, pp. 681–691 (1995); PDB entry 1LMW. The structure was refined using the XPLOR program package, A. Brunger, X-PLOR (version 2.1) Manual, Yale University, New Haven Conn. (1990).

Screening for Weak Bases

The μUK was screened against a structure-directed library in order to find a novel primary scaffold which would have favorable pharmacokinetic properties. Since the urokinase active site is composed of one primary pocket that contains a free carboxylate moiety in the form of an aspartic acid (Asp[189]), most well-known scaffolds are strongly basic and contain amidine or guanidine moieties. The basic group has been found to hydrogen bond salt-link with Asp[189]. This can be a problem pharmacologically since strong bases are known to decrease oral bioavailability. Accordingly, a weakly basic library containing compounds that were not previously known to be urokinase binders was selected.

A weak base library containing 61 compounds with pKa between about 1 and 9 was located in the available chemicals directory (ACD). The library was broken down into 9 mixtures of about 6 to 7 shape-diverse compounds, as determined by visual inspection of the two dimensional chemical structure. The compound mixtures were screened by the method described above. Specifically, each compound was dissolved in 100% DMSO to a final concentration of about 2M (or saturation for the less soluble). Equal volumes of each of the 6 or 7 compounds comprising the mixture were mixed to a final individual compound concentration of 0.33M. Single μUK crystals were placed in 50 ml of 27% PEG4000, 15.6 mM succinate pH 5.4, 0.17M $Li_2SO_4$ and 0.5–0.8 ml of the compound mixture added to give 1 to 1.6% DMSO and 3.3 to 5.2 mM final individual compound concentration. Under these conditions the sensitivity of the experiment is expected to detect binders with Kd<10 mM. Crystals were allowed to equilibrate for about 8–24 hrs.

Data were collected on a Rigaku RTP 300 RC rotating anode source with a RAXISII or MAR image plate detector. Typical data consisted of 45–50 2° oscillations with 2–5 min exposures. Typical data were 70–90% complete at 2.0–3.0 Å resolution with merging R-factors of 13–26%. Hence, the data quality ranged from fair to poor due to the rapid data collection protocol. However, this quality of data was shown to be adequate for the detection of binders primarily due to the high quality of the starting model which had been refined to 1.5 Å resolution (R=20.7% $R_{free}$=25.3%). Data were processed by the DENZO program package, Otwinowski et al., *Methods in Enzymology*, 276 (1996), and the electron density maps calculated by the XPLOR package.

Electron density maps were inspected on a Silicon Graphics INDIGO2 workstation using the QUANTA 97 program package (Molecular Simulations Inc., *Quanta Generating and Displaying Molecules*, San Diego: Molecular Simulations Inc., 1997). The shape of the density at the active site was visually identified as resulting from one (or more) of the compounds in the mixture indicating a positive hit or from ordered water molecules indicating the absence of binding. For experiments which resulted in a positive hit, the appropriate compound was visually moved into the electron density. The electron density maps were also checked for any changes in the protein structure and if observed, the appropriate modifications were made. Hence, after the map inspection/compound fitting step, the three-dimensional structure of the compound:protein complex was known. The urokinase example utilized visual movement of the compound into the density because the screening was still on a small scale. When expanded to larger scale compound screening, commercial programs such as the XFIT module of QUANTA will facilitate automatic fitting of the compound to the density.

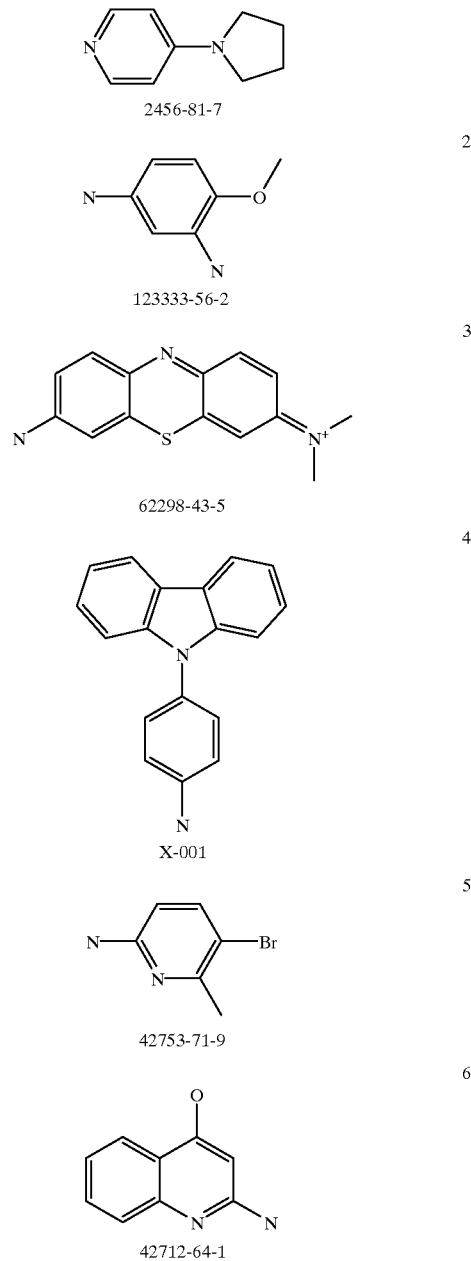

Figure 6:
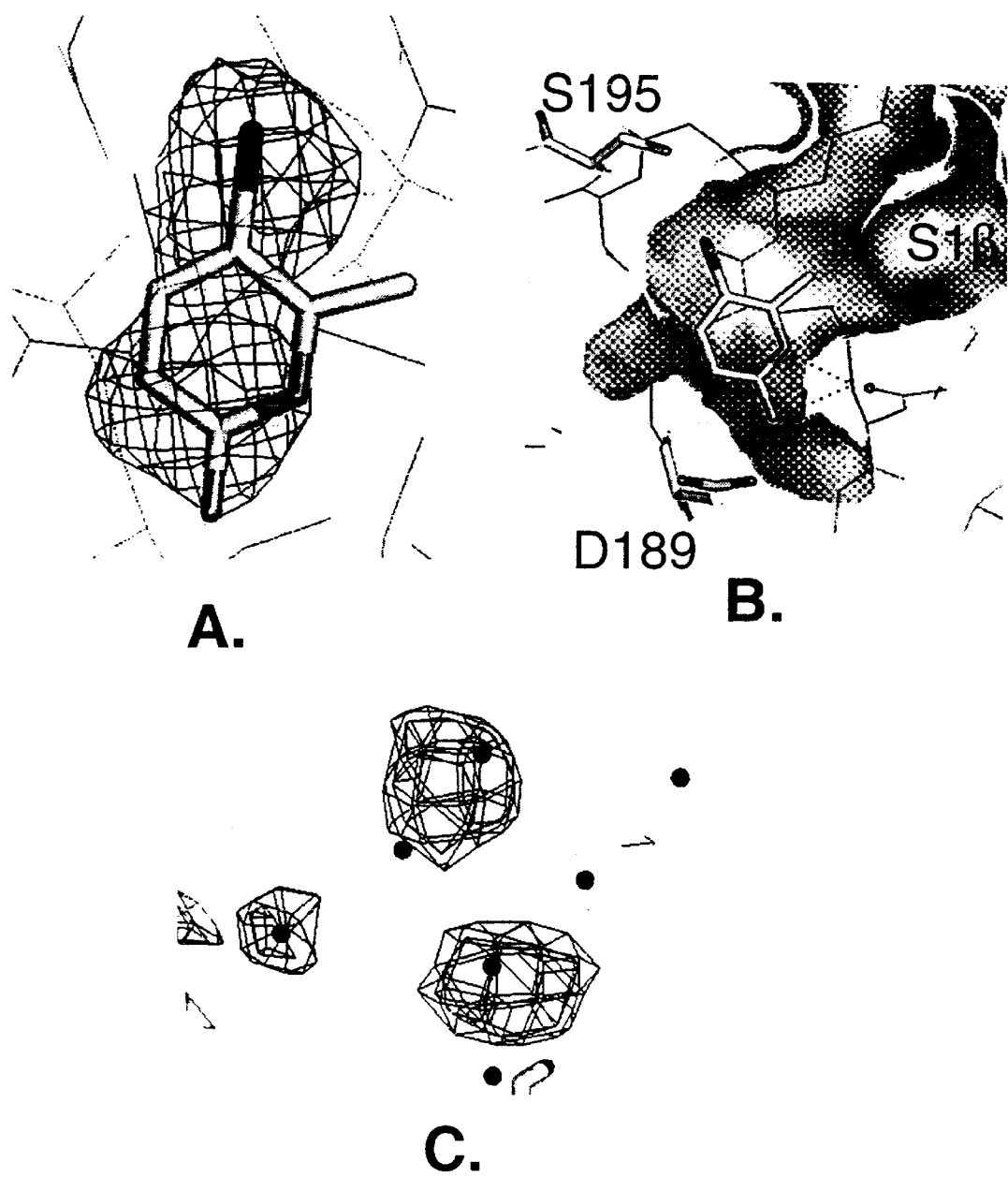
FIG. 6 illustrates how a hit was detected and identified by shape after urokinase was soaked in a solution containing a mixture of potential ligands.

FIG. 6 shows an example of a positive hit. The compounds screened are numbered 1 through 6 and the Fo-Fc electron density map at the active site is shown at FIG. 6A. The shape of the density identified the binder as compound 5. FIG. 6B shows the detailed binding mode of the compound in the primary specificity pocket as obtained directly by interpretation of the CrystaLEAD™ electron density map. The amino nitrogen hydrogen bonds with the Asp[189] carboxyl and the pyrimidyl nitrogen hydrogen bonds with a backbone carbonyl (Gly[218]). The structure also shows that the ideal site for modification would be at the pyridyl methyl.

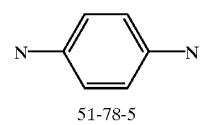

51-78-5

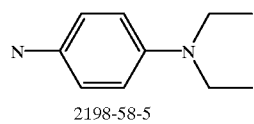

2198-58-5

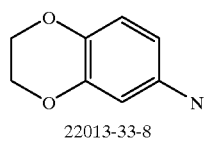

22013-33-8

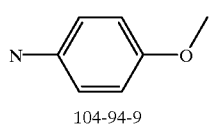

104-94-9

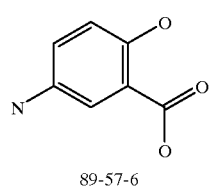

89-57-6

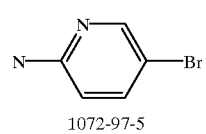

1072-97-5

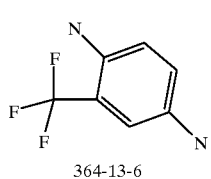

364-13-6

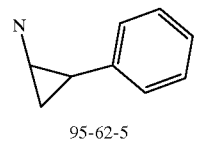

95-62-5

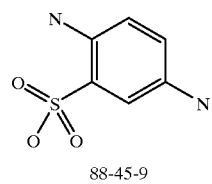

88-45-9

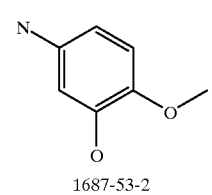

1687-53-2

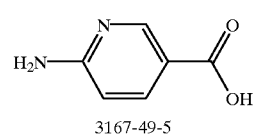

3167-49-5

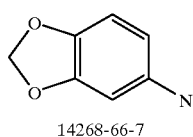

14268-66-7

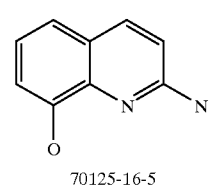

70125-16-5

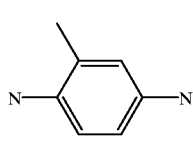

615-45-2

Another mixture of compounds (compounds 7 through 13) did not produce any hits. The resulting electron density map after soaking this group did not correspond to that of any of the tested compounds in this mixture. Instead, they correspond to bound solvent molecules. See FIG. 6C.

Figure 7:
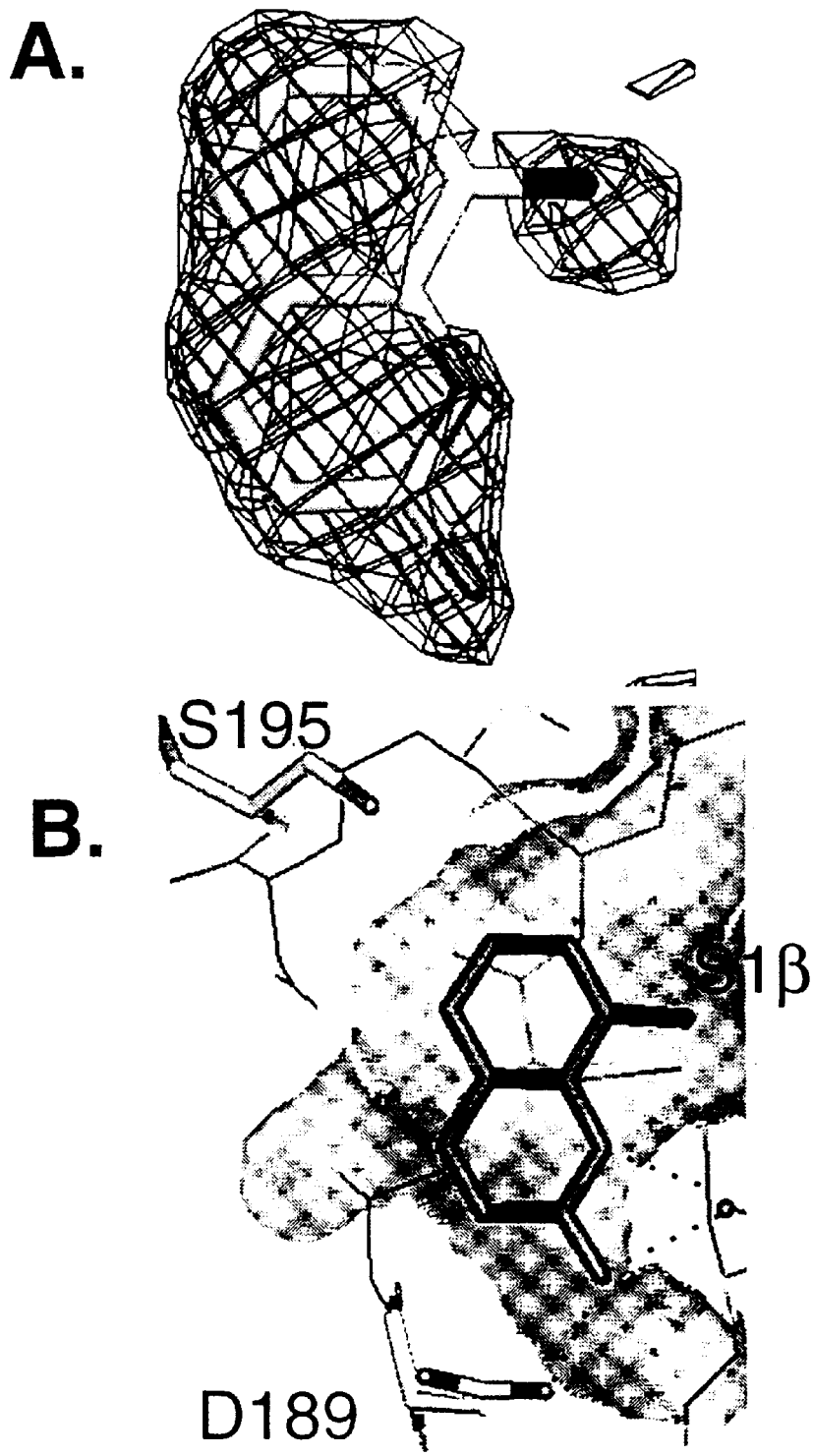
FIG. 7 illustrates a hit for urokinase soaked in a solution containing a mixture of potential ligands.
Figure 8:
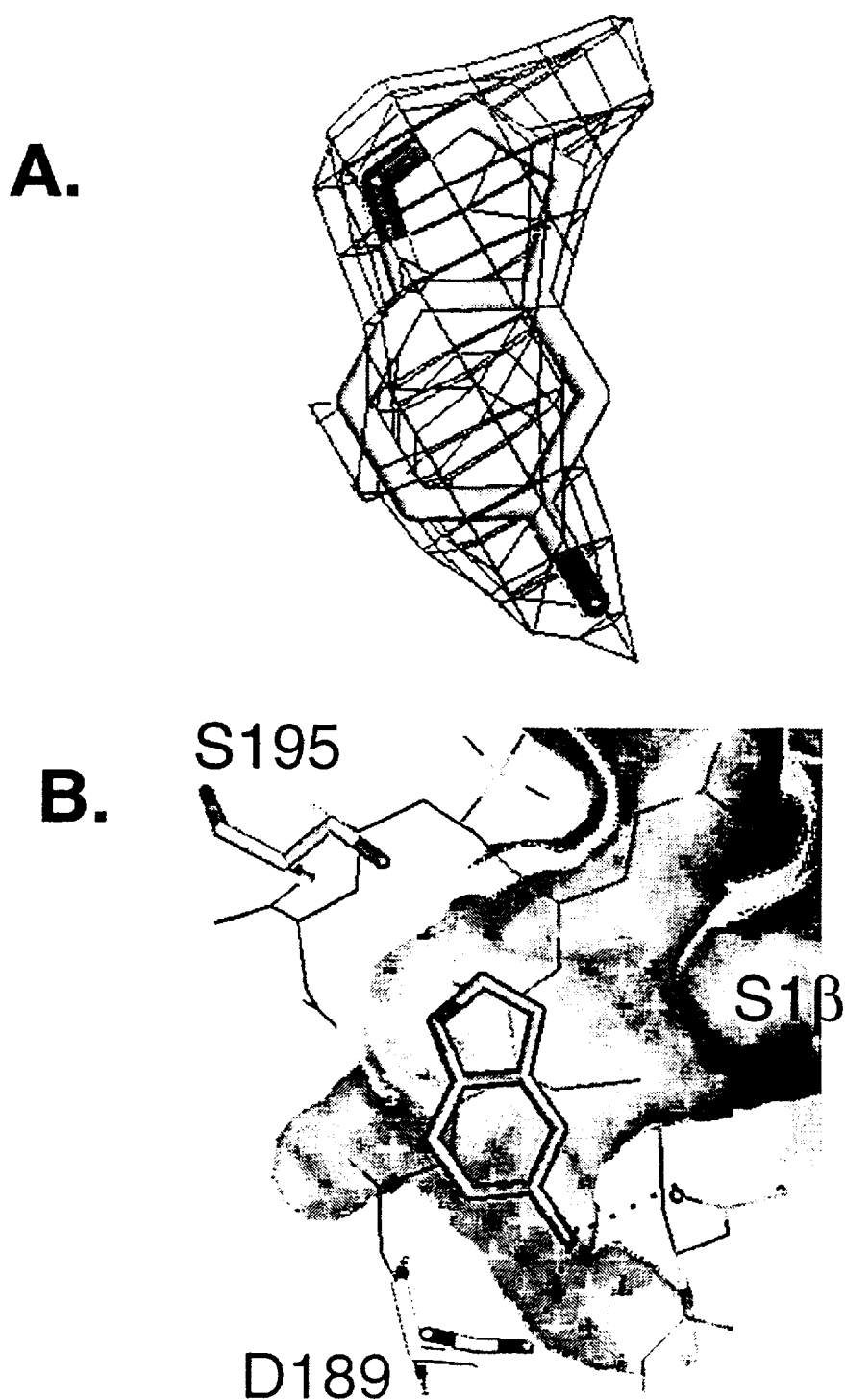
FIG. 8 illustrates a hit for urokinase soaked in a solution containing a mixture of potential ligands.

FIG. 7 shows another example of a positive hit. Of the seven compounds screened (14–20), the Fo-Fc map shown in FIG. 7A indicates that compound 19 is bound. The binding mode depicted in FIG. 7B shows that the 2-amino is hydrogen bonding with the Asp189 side chain and that the 8-hydroxyl is an ideal site for substitution in order to access the adjacent hydrophobic sub-pocket (denoted as S1β in FIG. 7B). FIG. 8 represents another hit where compound 22, 5-aminoindole, (FIG. 8A) was found to bind to urokinase with the amino group hydrogen bonding with Asp189 (FIG. 8B). Compounds screened were compounds 21–27.

application of the method, a library would be re-soaked in the absence of the tighter binder in order to detect weaker binders in the mixture, if desired.

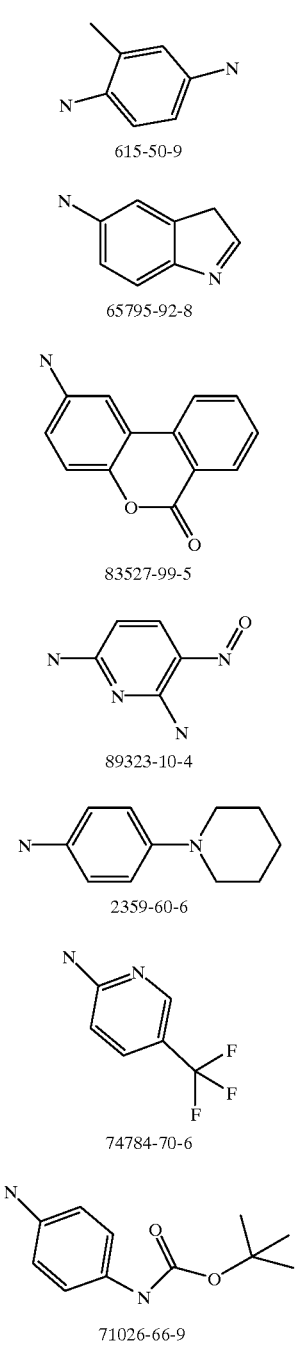

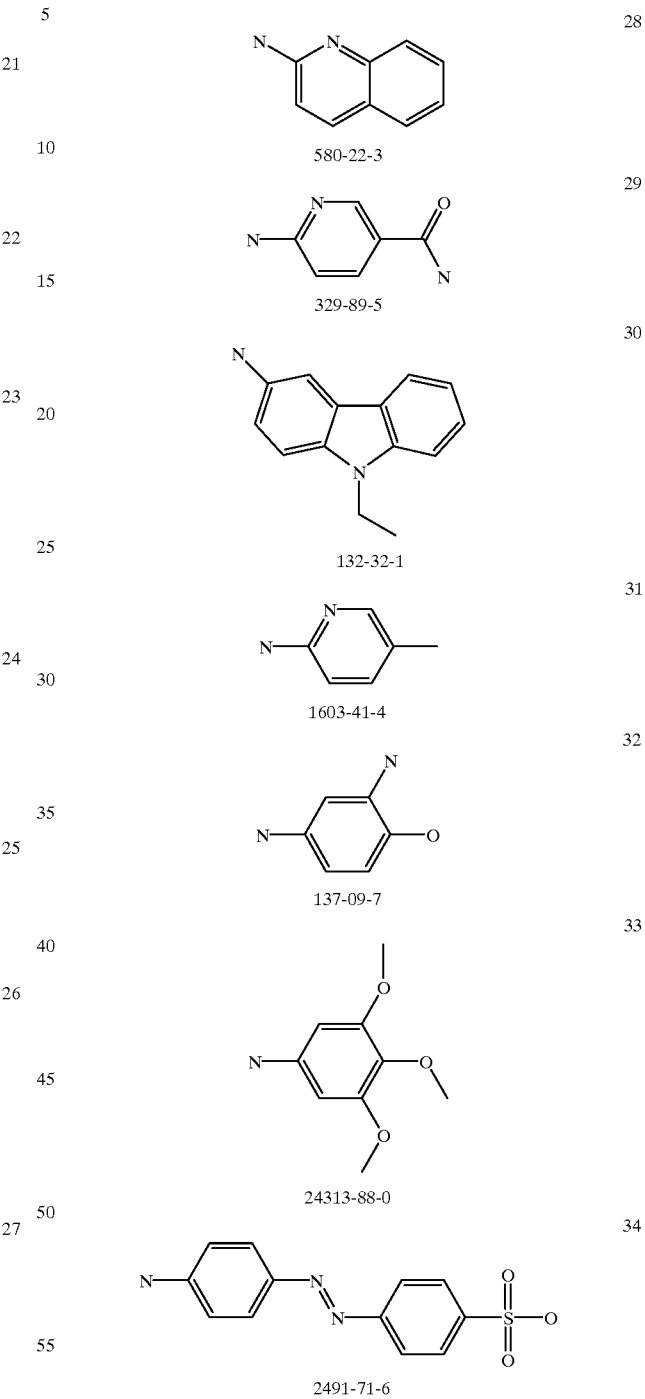

Figure 9:
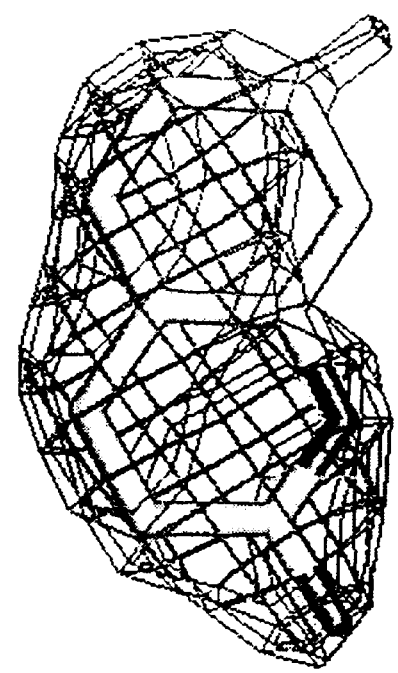
FIG. 9 illustrates two additional hits for urokinase soaked in a solution containing a mixture of potential ligands.
Figure 9:
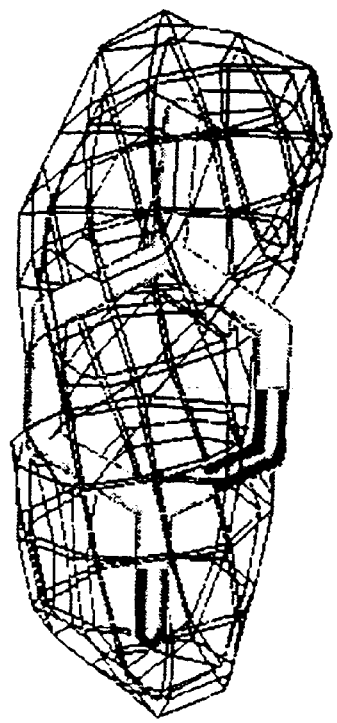

FIG. 9 shows an example where two compounds from the same mixture (compounds 28–34) were found to bind without multiple occupancy problems. In the initial experiment where the crystal was soaked in the presence of the entire compound mixture, compound 28 was found to bind (FIG. 9A). In addition, when the weaker binding compound 31 was soaked individually (based upon previous structure activity relationships established through CrystaLEAD™) it was also found to bind (FIG. 9B). In a more typical Table 1 summarizes the inhibition constants for each of the CrystaLEAD™ hits as determined by pyroGlu-Gly-Arg-pNA/HCl (S-2444, Chromogenix) chromogenic activity. Assays were completed at both pH 6.5 (0.1M NaPO$_4$) and 7.4 (50M Tris). Other conditions of the assay were 150 mM NaCl, 0.5% Pluronic F-68 detergent, 200 mM S-2444, with a final DMSO concentration of 2.5%. The Km of the substrate was determined to be 55 μM.

TABLE 1

Inhibition constants and pKa for hits detected by CrystaLEAD ™

| Compound (CAS #) | Ki (pH 6.5) | Ki (pH 7.4) | pKa |
|---|---|---|---|
| 5 (42753-71-9) | >>500 µM | >>500 µM | 6.0* |
| 19 (70125-16-5) | 56 µM | 137 µM | 7.3 |
| 22 (65795-92-8) | 200 µM | >500 µM | 6.0* |
| 28 (580-22-3) | 71 µM | 136 µM | 7.3 |
| 31 (1603-41-4) | >>500 µM | 500 µM | 7.0* |

*indicates estimated pKa

Based upon the activity and structural information, compound 19 was chosen as the lead compound. Crystallographic information indicated that substitution at the 8-position should allow access to the adjacent hydrophobic pocket (S1β) pocket and thereby result in an increase in potency. Based upon crystallographic and binding information from an amidine-based series, compound 35 was synthesized (the 8-aminopyrimidinyl analog of compound 19). This modification resulted in about a 200 fold increase in binding potency at pH 6.5 (Ki pH7.4=2.5 µM; Ki pH6.5= 0.32 µM). The experiment indicates that CrystaLEAD™ can provide both a lead scaffold and the detailed structural information necessary to elaborate that scaffold through structure-based drug design into a more potent compound.

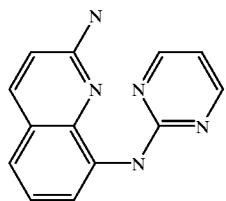

35

Figure 10:
FIG. 10 illustrates the comparative crystal structures between a lead compound found by CrystaLEAD™ and an optimized follow-up compound.

In FIG. 10, an overlay of the crystal compound 35:urokinase and the parent compound 19 are shown. The overlay shows that the aminopyridine ring is bound in the hydrophobic sub-pocket (S1β) pocket as predicted and that this substitution results in movement of the quinoline ring towards this site.

Compound 35, the 8-aminopyrimidinyl-2-aminoquinoline, was also tested for oral bioavailability. Compound 35 was determined to be 30–40% orally bioavailable in the rat when administered at a 10 mg/kg dose. Hence, successful implementation of CrystaLEAD™ resulted in a novel lead scaffold which through one cycle of structure-based drug design produced a compound having a 200-fold increase in potency, and was found to be orally bioavailable.

Example 2

VanX

Vancomycin is the drug of choice for infections caused by streptococcal or staphylococcal bacterial strains that are resistant to β-lactam antibiotics. However, strains of vancomycin resistant bacteria have now been found for this drug of last recourse. Some investigators have associated VanX, a metalloproteinase, with vancomycin resistance. VanX is part of a cascade that results in replacement of the terminal D-Ala-D-Ala moiety of the bacterial peptidoglycan chain (the binding site for vancomycin) with a D-Ala-D-lactate. This results in a 1000-fold decrease in vancomycin binding. The only known inhibitors of VanX are peptides or peptide derivatives, such as phosphonate or phosphinate analogs of the D-Ala-D-Ala substrate. As such, they are not suitable drugs because they are metabolized and/or degraded in vivo. Initial attempts to find suitable drugs by normal screening methods did not uncover a suitable ligand. Subsequently, Applicants turned to CrystaLEAD™ to find a non-peptide lead compound for drug development towards a treatment for these resistant strains.

VanX Preparation

*E. coli* W3110 containing plasmid pGW1, in which the vanX gene is under control of the IPTG-inducible tac promoter, was grown at 37° C. in LB medium containing ampicillin (100 µg/ml) to an absorbance of about 1.3–1.5 at 595 nm. Then IPTG was then added to a final concentration of 0.8 mM, and the cells were grown for an additional 1.5 hours.

Cells were harvested by centrifugation at 6000 rpm for 10 min. Then, the pellet was resuspended in ice cold 20 mM Tris-HCl (pH 8.0) containing 0.01% $NaN_3$, 1 mM $MgCl_2$, 1 mM PMSF, 1 mM DTT (Buffer A) and 25 units/ml of benzonase (Nicomed Pharma, Copenhagen, Denmark). The cells were lysed by the addition of 0.1 micron zirconia ceramic beads to the lysate mixture (1:1 v:v) with a 1–3 minute run in a Bead Beater (Biospec), an ultrasound bead mill. The Bead Beater was run with an ice-packed reservoir to maintain a chilled lysate. Then, the lysate was decanted away from the settled glass beads. The beads were then rinsed with 1–2 volumes of lysis buffer, and the washes were then pooled with the original lysate. The lysate was centrifuged at 25000 g for 30 minutes to settle cell debris. The supernatant was dialyzed overnight at 4° C. in 50 mM Tris-HCl, pH 7.6, 1 mm EDTA, and 1 mM DTT (Buffer B).

Thereafter, the dialyzed lysate was loaded onto a Q-sepharose fast flow column, pre-equilibrated in Buffer A at a rate of four millimeters per minute. The column was exhaustively washed with the Buffer A followed by a linear gradient of Buffer B to Buffer B+0.5M NaCl. The active VanX fractions from this step were pooled, concentrated and then applied to a Superose-75 column in Buffer B. VanX fractions from the Superose column run were then applied to a Source-Q column in Buffer A at a flow rate of 2 ml/min. The column was washed with starting buffer for several column volumes. Then the VanX protein was eluted off with a shallow gradient of Buffer A to Buffer A+25 mM NaCl. The active VanX fractions from this final step were concentrated to a final concentration of approximately 15 mg/ml in Buffer A with Amicon filters. Unless otherwise specified, the foregoing procedure was run at 4° C. As purified, the VanX protein was approximately 95% pure and readily crystallized.

VanX Crystal Structure

The crystal structure of VanX was determined at 2.2 Å resolution by multiple isomorphous replacement. Bussiere et al., *Molecular Cell*, Vol. 2, pp 75–84 (1998). The recombinant protein obtained above was crystallized in the space group $P2_1$ by the sitting drop vapor diffusion method. Typical crystals had unit cell dimensions of a=83.4 Å, b=45.5 Å, c=171.4 Å, α=γ=90°, β=104° with six molecules in the asymmetric unit. Typical well solutions consist of 0.1M Mes pH 6.4, 0.24M ammonium sulfate, and 20% PMME 5000. On the sitting drop microbridge (Hampton USA), 2 ml of protein are mixed with 2 ml of well solution and the chamber sealed with a cover slip. Crystallization occurs at 18° C., and the crystals grow to full size in about 2–3 days. The protein solution is composed of 12–15 mg/ml (0.5–0.6 mM) VanX in 10 mM Tris, 15 mM DTT, pH 7.2. The 3-D structure for crystals grown under these conditions show an empty active site making this a system highly suitable for application of CrystaLEAD™.

The VanX active site has an extended pocket capable of accommodating the D-Ala-D-Ala substrate. The pocket also contains a catalytic zinc. Thus, for this case, VanX was initially screened against zinc directed libraries in order to find multiple binding scaffolds which could be merged into a single lead compound. Three libraries utilizing amino-acid, thiol, hydroxamic acid or carboxylate moieties directed towards zinc were screened.

Screening

The amino acid library consisted of 102 compounds of optically pure commercially available natural and non-naturally occurring amino acids. The library was divided into 12 mixtures of 8–10 shape-diverse compounds and screened by the method described above. Specifically, each compound was dissolved in 100% DMSO to a final concentration of 2M (or saturation for the less soluble). Equal volumes of each compound of each mixture were mixed to a final individual compound concentration of 0.33M. Single VanX crystals were placed in 50 ml of 0.1M Mes pH 6.4, 0.24M ammonium sulfate, 20% PMME 5000 and 0.5–0.8 ml of the compound mixture added to give 1 to 1.6% DMSO and 3.3 to 5.2 mM final individual compound concentration. Crystals were allowed to equilibrate for 3–4 hrs. The thiol, hydroxamic and carboxylate libraries were prepared and screened in a similar manner.

Data were collected on a Rigaku RTP 300 RC rotating anode source with a RAXISII, MAR image plate, or MAR CCD detector. For the image plate systems, typical data consisted of 90 1.25° oscillations with 15 min exposures while for the CCD 100 1.0° oscillations were exposed for two minutes. Typical usable data were >90% complete at 2.6–2.8 Å resolution with merging R-factors of 10–20%. This was required to adequately visualize and identify inhibitors in the Fo-Fc or 2Fo-Fc maps. For these maps, the starting model had been refined to 2.1 Å resolution (R=25% $R_{free}$=28%). Data were processed by the DENZO program package and the electron density maps calculated by the XPLOR package. In the presence of some compounds of the carboxylate library, the space group was shown to shift from P2$_1$ to C2 (a=170.6 Å, b=47.5 Å, c=83.6 Å, α=γ=90°, β=104°). For this form, the asymmetric unit contained a trimer thereby reducing the number of degrees of freedom so that lower resolution data (3.0 Å) were adequate for visualization of binding.

Electron density maps were inspected on a Silicon Graphics INDIGO2 workstation using QUANTA 97. The shape of the density at the active site was visually identified by the shape of one or more of the compounds in the mixture to indicate a positive hit or by ordered water molecules indicating the absence of binding. For experiments which resulted in a positive hit, the appropriate compound was visually moved into the electron density. The electron density maps were also checked for any changes in the protein structure, and if observed, corresponding modifications were made in the structure. Hence, after the map inspection/compound-fitting step, the detailed 3-D structure of the compound:protein complex was known.

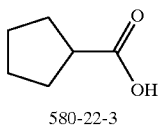

580-22-3

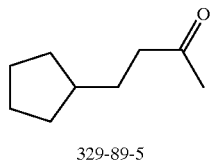

329-89-5

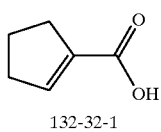

132-32-1

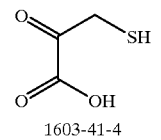

1603-41-4

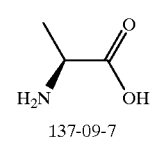

137-09-7

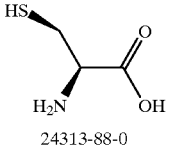

24313-88-0

Figure 11:
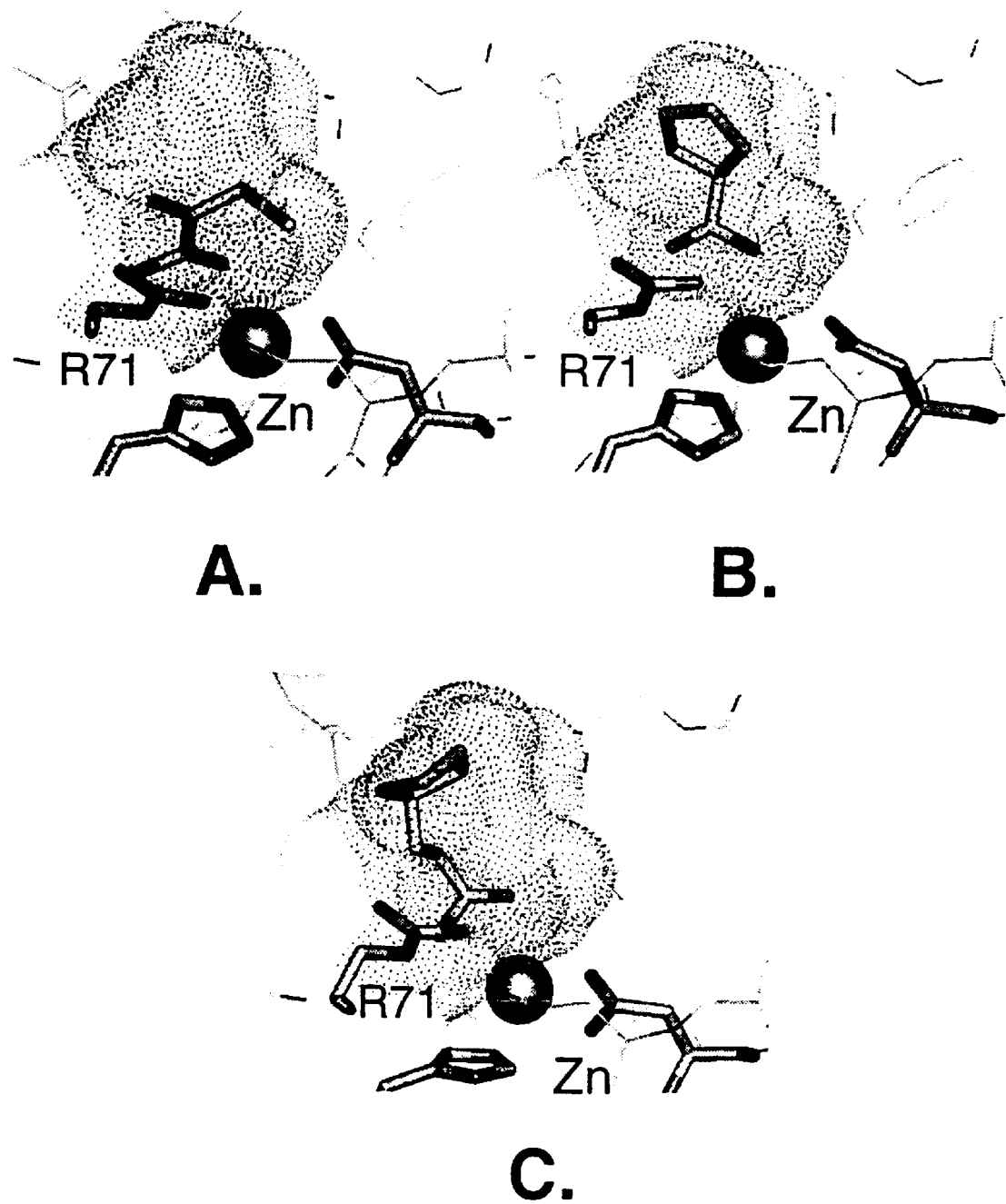
FIG. 11 illustrates hits that were identified for VanX.

Currently 6 hits have been detected in the VanX screens (compounds 36–41). FIG. 11 shows the binding mode of representative hits. In all cases, the electron density shape identified the binding compound. FIG. 11A shows compound 39 bound with the carboxylate coordinating to the active site zinc. FIG. 11B, shows compound 36 bound with the carboxylate pointing towards the active site zinc. In FIG. 11C, compound 37 was also found to bind through the carboxylate. The binding of compound 39 and compound 41 (not shown) suggests that the active site zinc prefers coordination of a carboxylate over a free thiol. This led to screening of a carboxylate library where additional hits were found. In all cases, the compounds were screened in mixtures of 7–10 and the hit directly identified by the shape of the electron density map. These hits are fed directly into the structure-based drug design cycle in a manner similar to that described for the urokinase example.

Example 3

Screening with Mixtures of 100 Compounds

In order to increase the number of compounds that may be screened per unit time by the CrystaLEAD™ method, a preferred embodiment of the method would be to screen mixtures of 100 compounds rather than mixtures of 10. The advantage of this method is a higher compound throughput with a concurrent lowering of the sensitivity of the hit detection. In addition, since only the most potent compound in a mixture will bind, weaker hits may be missed. When a general library, for example, one which is fully diverse in size, shape and functionality, is screened by CrystaLEAD™, the hit-rate is expected to be low. Therefore, a more coarse screen is warranted. In addition, since the hits from this screen would be the more potent binders, they could serve as starting scaffolds for structure-based drug design. Since the compound mixture will be composed of 100 compounds, the mixture should be carefully designed in order to ensure that all members would be diversely shaped enough to eliminate the need for deconvolution. Hence, upon hit detection, some deconvolution may be necessary to identify the hit.

To test this particular method, a compound known to bind to μUK was added to a group of 100 compounds. This known binder, compound 19, was originally discovered by the CrystaLEAD™ method and shown to bind to μUK with a Ki of 56 μM at pH 6.5 and 137 μM at pH 7.4. The 100 compound mixture was constructed by mixing 10 mixtures of 10 compounds. Specifically, each dry mixture of 10 was dissolved in 100% DMSO to a final concentration of about 80–240 mM(or saturation for the less soluble). Equal volumes of each of the mixtures of 10 compounds were mixed to a final individual compound concentration of 8.0–24.0 mM and the mixture spiked with a 100% DMSO stock of compound 19 such that the final concentration was 18.0 mM. Single μUK crystals were placed in 50 μl of 27% PEG4000, 15.6 mM succinate pH 5.4, 0.17M $Li_2SO_4$ and 0.5 μLof the compound mixture added to give 1% DMSO. The final concentration of each compound in the soak experiment ranged from 80–240 μM, the concentration of compound 19 was 180 μM. Under these conditions the sensitivity of the experiment is expected to detect binders with Kd<20–60 μM. Crystals were allowed to equilibrate for 4 hours and 15 minutes.

Data were collected at the Argonne National Labs advanced photon source synchrotron ID beamline IMCA equipped with a MarCCD camera. Data consisted of 100 1° oscillations with 7 sec exposures. Data were 87.4% complete at 1.6 Å resolution with an overall merging R-factor of 5.4%. Data were processed by the DENZO program package, Otwinowski et al., *Methods in Enzymology*, 276 (1996), and the electron density map calculated by the XPLOR package.

Figure 12:
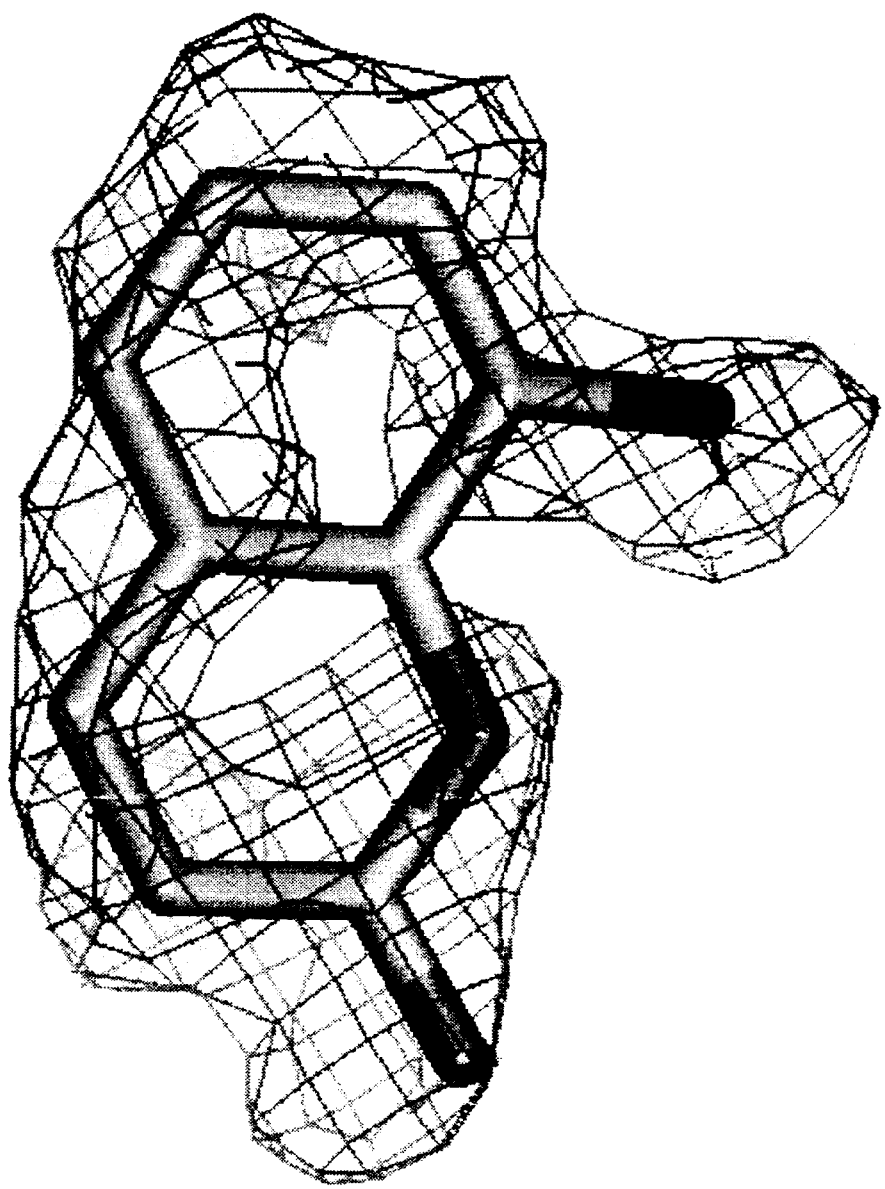
FIG. 12 illustrates a hit for urokinase.

The electron density map was inspected on a Silicon Graphics INDIGO2 workstation using the QUANTA 97 program package (Molecular Simulations Inc., *Quanta Generating and Displaying Molecules*, San Diego: Molecular Simulations Inc., 1997). The shape of the density at the active site was visually identified as resulting from one of the compounds in the mixture indicating a positive hit which was identified as compound 19, and is illustrated in FIG. 12.

This method is preferable for discovering lead compounds. Lead compounds would typically have the characteristics of being tighter binders (for example, within the sensitivity range of the method). This method also allows screening of a 10,000 compound non-directed library on the timeframe of 1–2 weeks. This method would be used in conjunction with the other methods of screening 10–20 compounds at a time where weaker binders would be identified. These binders would be less likely to serve as lead compounds, but could be attached to a lead scaffold in order to increase the potency.

Example 4

CrystaLEAD™ Screening of ErmC'

ErmC' is an rRNA methyltransferase that transfers a methyl group from S-Adenosyl-L-methionine to N6 of adenine within the peptidyltransferase loop of 23S rRNA. This methylation confers antibiotic resistance against a number of macrolide antibiotics such as the widely prescribed erythromycin. Inhibition of ErmC' would be expected to reverse resistance. In order to design a specific and potent ErmC' inhibitor, the cofactor or S-Adenosyl-L-methionine binding site has been targeted. S-Adenosyl-L-methionine is illustrated below as compound 42:

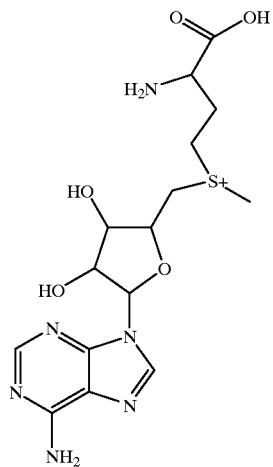

42

The crystal structure of ErmC' shows that the S-Adenosyl-L-methionine site is composed of two primary pockets which accommodate the adenine ring and the methionine. In addition, there is a third pocket which may accommodate the rRNA adenine that undergoes methylation. In order establish an SAR at this site, a library of adenosine analogues substituted at N6 and/or 5' hydroxyl was generated. The sites of variation in the library is represented below as compound 43.

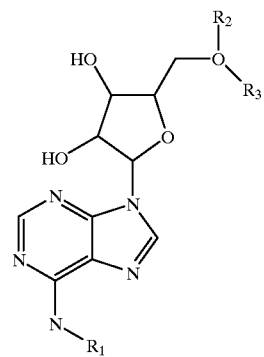

43

ErmC Expression and Purification

The expression vector pTERM31 was constructed by polymerase chain reaction (PCR) amplification of the ermC' gene and the upstream kdsB cistron from pERM-1. Subcloning the PCR product into pET24+ (Novagen, Madison, Wis.) was performed using the BamHI and HindIII sites included in the "tailed" PCR primers. This new construct allowed the expression of ErmC' by translational coupling to kdsB, under the control of the T7lac promoter. pTERM31 plasmid was transformed into *E. coli* strain BL219(DE3)/pLysS (Novagen) and the resulting strain was used for production of ErmC'. Transformed cells were grown at 27.5°

C. in a New Brunswick Scientific (Edison, N.J.) Micros fermentor containing 10 l of Superbroth (BIO 101, La Jolla, Calif.), supplemented with kanamycin, chloramphenicol, and glucose. When the culture optical density reached 1.10, ErmC' expression was induced by the addition of 1 mM isopropyl β-d-thiogalactopyranoside (IPTG). Cells were harvested 400 minutes post-induction.

Frozen cell paste (200–250 g) was thawed at room temperature and resuspended into 5–10 volumes of cold lysis buffer (50 mM Tris, 5 mM 1,4-dithiothreitol (DTT), 1 mM phenylmethylsulfonate fluoride (PMSF), 2 mM ethylene-diaminetetraacetic acid (EDTA), 0.2% Triton X-100, ph 7.8). The cells were lysed with a French press and cell debris removed by centrifugation. The supernatant was dialysed overnight against 20 l Tris-DTT-glycerol-magnesium (TDGM) buffer, pH 7.8 (50 mM Tris, 5 mM DTT, 10% glycerol, 10 mM MgCl12). The dialysate was then applied to a Sepharose Fast Flow column (Pharmacia) that had been pre-equilibrated in TDGM buffer. Fractions were assayed for methyltransferase activity and those containing ErmC' were pooled, applied to a TSK SP-5PW column (TosoHaas, Montgomeryville, Pa.), and eluted with an NaCl gradient. The purified protein was then concentrated on a YM-10 (Amicon) membrane.

ErmC Crystal Structure

Crystals of ErmC' were grown by the hanging drop vapor diffusion method. Drops containing 5–8 mgs/ml ErmC' in 25 mM Tris/Cl, 100 mM NaCl, 2 mM DTT, 10% (v/v) glycerol, pH 7.5 were equilibrated against a reservoir containing 100 mM Tris, 500 mM NH4(SO)4, 15% PEG 8000, pH 7.8. Crystals appeared within one day and grew to their full size within one week. Crystals belonged to the space group P43212. The structure of ErmC' in this space group was determined by molecular replacement to 2.2 angstrom resolution using the crystal structure of ErmC' in the space group P6 (Bussiere et al., Biochemistry Vol. 37, pp 7103–7112). The 3-D structure for crystals grown under these conditions show an empty active site making this a system highly suitable for application of CrystaLEAD™.

Screening

The adenosine library consisted of 59 compounds. The library was divided into 7 mixtures of 8–9 shape-diverse compounds and screened by the CrystaLEAD™ method. Specifically, each compound was dissolved in 100% DMSO to a final concentration of 1M (or saturation for the less soluble). Equal volumes of each compound were mixed to assemble the mixture of 10. Single ErmC crystals were placed in 50 μl of 20% PEG 8000, 0.3M ammonium sulfate, 10% glycerol, pH 7.7 and 0.5–0.8 μl of the compound mixture added to give 1 to 1.6% DMSO and 3.3 to 5.2 μM final individual compound concentration. Crystals were allowed to equilibrate for 3–4 hrs.

Data were collected on a Rigaku RTP 300 RC rotating anode source with a RAXISII, MAR image plate, or MAR CCD detector. For the image plate systems, typical data consisted of 15–20 2° oscillations with 20–30 min exposures while for the CCD 15–20 2.0° oscillations were exposed for 8–15 minutes. Typical usable data were 80–90% complete at 3.4–3.6 Å resolution with merging R-factors of 7–16%. This was required to adequately visualize and identify inhibitors in the Fo-Fc or 2Fo-Fc maps. For these maps, the starting model had been refined to 2.2 Å resolution (R=22% $R_{free}$=25%). Data were processed by the DENZO program package and the electron density maps calculated by the XPLOR package.

Electron density maps were inspected on a Silicon Graphics INDIGO2 workstation using QUANTA 97. The shape of the density at the active site was visually identified by the shape of one or more of the compounds in the mixture to indicate a positive hit or by ordered water molecules indicating the absence of binding. For experiments which resulted in a positive hit, the appropriate compound was visually moved into the electron density. The electron density maps were also checked for any changes in the protein structure, and if observed, corresponding modifications were made in the structure. Hence, after the map inspection/compound-fitting step, the detailed 3-D structure of the compound:protein complex was known.

Figure 13:
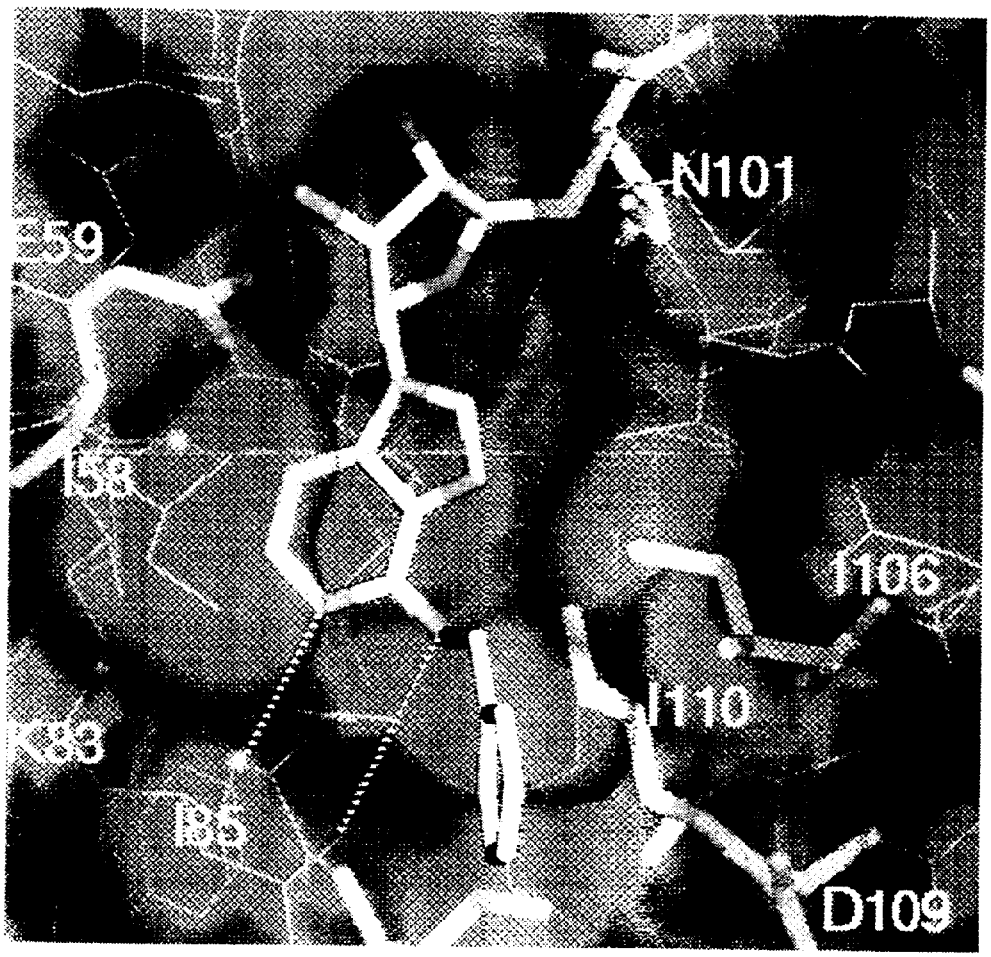
FIG. 13 illustrates the crystal structure of compound 44 with ErmC'.
Figure 14:
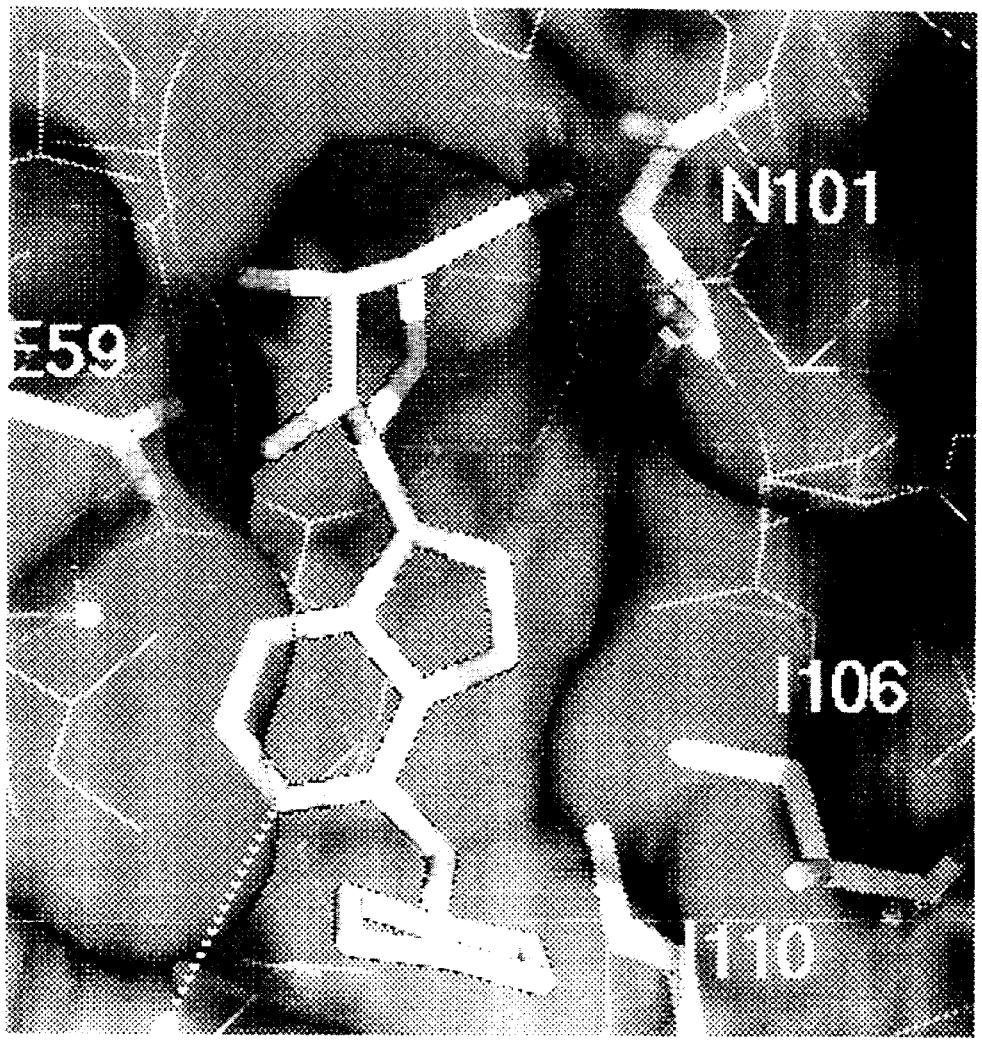
FIG. 14 illustrates the crystal structure of compound 45 with ErmC'.

Two hits were detected in the ErmC' adenosine analogue screen (compounds 44 and 45). FIGS. 13 and 14 show the crystal structure of the complexes of compounds 44 and 45 with ErmC'.

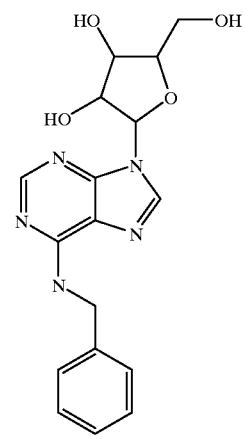

44

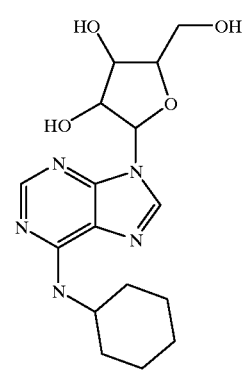

45

In all cases, the electron density shape identified the binding compound. The hydrophobic substitution was found to bind along a partially exposed hydrophobic surface suggesting a preferred interaction which may have contributed to the binding of these compounds, allowing them to be pulled out as hits. No hits containing a substitution at the 5'OH position were detected. A follow-up compound to compounds 44 and 45 contained an optimized indane substituent at this hydrophobic site.

We claim:

1. A process for identifying a ligand which binds to a target biomolecule comprising the steps of:
   a) exposing a target biomolecule to a mixture of at least two potential ligands;
   b) attempting to crystallize said target biomolecule with exposure to said mixture;
   c) if crystals are obtained, obtaining an X-ray diffraction pattern of said target biomolecule crystal with exposure to said mixture; and
   d) determining whether a ligand/target biomolecule complex is formed by comparing the X-ray diffraction pattern of said target biomolecule crystal when exposed to said mixture of said at least two potential ligands to the X-ray diffraction pattern of the target biomolecule crystal obtained when not exposed to said mixture of said at least two potential ligands.

2. The process according to claim 1 further comprising the step of converting said target biomolecule diffraction patterns into electron density maps using known phases of said target biomolecule crystal and comparing said electron density maps without exposure to said mixture and with exposure to said mixture to determine whether a ligand/target biomolecule complex is formed.

3. The process according to claim 1 wherein said ligands in said mixture are diversely shaped at the molecular level.

4. The process according to claim 1 wherein at least one of said ligands in said mixture is a biologically-active moiety.

5. A biologically active moiety identified by the process according to claim 4.

6. The process according to claim 1 wherein the target biomolecule is a polypeptide.

7. The process according to claim 1 wherein the target biomolecule is a polypeptide other than a native polypeptide.

8. The process according to claim 1 wherein at least one of said ligands in said mixture is a lead compound.

9. A process for identifying a ligand which binds to a target biomolecule, wherein said target biomolecule forms crystals when bound to a ligand and wherein said target biomolecule does not form crystals when unbound to a ligand, said process comprising the steps of:
   a) exposing a target biomolecule to a mixture of at least two potential ligands;
   b) attempting to crystallize said target biomolecule in the presence of said mixture; and
   c) obtaining a crystal of said target biomolecule exposed to said mixture to determine whether a ligand/target biomolecule complex is formed.

10. The process according to claim 9 wherein said ligands in said mixture are diversely shaped at the molecular level.

11. The process acording to claim 9 wherein at least one of said ligands in said mixture is a biologically-active moiety.

12. A biologically active moiety identified by the process acording to claim 11.

13. The process according to claim 9 wherein the target biolecule is a polypeptide.

14. The process according to claim 9 wherein the target biolecule is a polypeptide other than a native polypeptide.

15. The process acording to claim 9 wherein at least one of said ligands in said mixture is a lead compound.

16. A process for identifying a ligand which binds to a target biomolecule, wherein said target biomolecule forms crystals when bound to a ligand and wherein said target biomolecule does not form crystals when unbound to a ligand, said process comprising the steps of:
   a) exposing a target biomolecule to a mixture of at least two potential ligands;
   b) attempting to crystallize said target biomolecule with exposure to said mixture;
   c) if crystals are obtained, obtaining an X-ray diffraction pattern of said target biomolecule crystal with exposure to said mixture; and
   d) converting said X-ray diffraction pattern of said crystal into an electron density map using known phases of said target biomolecule crystal and determining whether a ligand/target biomolecule complex is formed from said electron density map.

17. The process according to claim 16 wherein said ligands in said mixture are diversely shaped at the molecular level.

18. The process according to claim 16 wherein at least one of said ligands in said mixture is a biologically-active moiety.

19. A biologically active moiety identified by the process according to claim 18.

20. The process according to claim 16 wherein the target biomolecule is a polypeptide.

21. The process according to claim 16 wherein the target biomolecule is a polypeptide other than a native polypeptide.

22. The process according to claim 16 wherein at least one of said ligands in said mixture is a lead compound.

* * * * *

SEQUENCE LISTING

<160> NUMBER OF SEQ ID NOS: 14

<210> SEQ ID NO 1
<211> LENGTH: 51
<212> TYPE: DNA
<213> ORGANISM: Synthetic

<400> SEQUENCE: 1
attaatgtcg actaaggagg tgatctaatg ttaaaatttc agtgtggcca a        51

<210> SEQ ID NO 2
<211> LENGTH: 57
<212> TYPE: DNA
<213> ORGANISM: Synthetic

<400> SEQUENCE: 2
attaataagc tttcagaggg ccaggccatt ctcttccttg gtgtgactcc tgatcca   57

<210> SEQ ID NO 3
<211> LENGTH: 47
<212> TYPE: DNA
<213> ORGANISM: Synthetic

<400> SEQUENCE: 3
attaattgcg cagccatccc ggactataca gaccatcgcc ctgccct              47

<210> SEQ ID NO 4
<211> LENGTH: 46
<212> TYPE: DNA
<213> ORGANISM: Synthetic

<400> SEQUENCE: 4
attaatcagc tgctccggat agagatagtc ggtagactgc tctttt               46

<210> SEQ ID NO 5
<211> LENGTH: 28
<212> TYPE: DNA
<213> ORGANISM: Synthetic

<400> SEQUENCE: 5
attaatcagc tgaaaatgac tgttgtga                                   28

<210> SEQ ID NO 6
<211> LENGTH: 51
<212> TYPE: DNA
<213> ORGANISM: Synthetic

<400> SEQUENCE: 6
attaatgtcg actaaggagg tgatctaatg ttaaaatttc agtgtggcca a        51

<210> SEQ ID NO 7
<211> LENGTH: 37
<212> TYPE: DNA
<213> ORGANISM: Synthetic

<400> SEQUENCE: 7
attaatgcta gcctcgagcc accatgagag ccctgct                         37

<210> SEQ ID NO 8
<211> LENGTH: 42
<212> TYPE: DNA
<213> ORGANISM: Synthetic

-continued

```
<400> SEQUENCE: 8
attaatgcta gcctcgagtc acttgttgtg actgcggatc ca                42

<210> SEQ ID NO 9
<211> LENGTH: 44
<212> TYPE: DNA
<213> ORGANISM: Synthetic

<400> SEQUENCE: 9
ggtggtgaat tctcccccaa taatgccttt ggagtcgctc acga              44

<210> SEQ ID NO 10
<211> LENGTH: 111
<212> TYPE: DNA
<213> ORGANISM: Yeast Pichia Pastoria

<400> SEQUENCE: 10
atgttctctc caattttgtc cttggaaatt attttagctt tggctacttt gcaatctgtc   60
ttcgctcagc cagttatctg cactaccgtt ggttccgctg ccgagggatc c          111

<210> SEQ ID NO 11
<211> LENGTH: 22
<212> TYPE: DNA
<213> ORGANISM: Synthetic

<400> SEQUENCE: 11
gaaacttcca aaagtcgcca ta                                     22

<210> SEQ ID NO 12
<211> LENGTH: 92
<212> TYPE: DNA
<213> ORGANISM: Synthetic

<400> SEQUENCE: 12
attaatgaat tcctcgagcg gtccgggatc cctcggcagc ggaaccaacg gtagtgcaga   60
taactggctg agcgaagaca gattgcaaag ta                            92

<210> SEQ ID NO 13
<211> LENGTH: 46
<212> TYPE: DNA
<213> ORGANISM: Synthetic

<400> SEQUENCE: 13
attaatggat ccttggacaa gaggattatt gggggagaat tcacca            46

<210> SEQ ID NO 14
<211> LENGTH: 47
<212> TYPE: DNA
<213> ORGANISM: Synthetic

<400> SEQUENCE: 14
attaatctcg agcggtccgt cacttggtgt gactgcgaat ccagggt           47
```